US012642484B2

(12) United States Patent
Sarnow et al.

(10) Patent No.: US 12,642,484 B2
(45) Date of Patent: *Jun. 2, 2026

(54) SYSTEM AND METHOD FOR DETERMINING A SUBJECT'S MUSCLE FUEL LEVEL, MUSCLE FUEL RATING, AND MUSCLE ENERGY STATUS

(71) Applicant: MUSCLESOUND, INC., Glendale, CO (US)

(72) Inventors: Pierre Sarnow, Littleton, CO (US); Stephen S. Kurtz, Englewood, CO (US); Andrew D. Jackson, Denver, CO (US); Wayne Phillips, Gilbert, AZ (US)

(73) Assignee: MUSCLESOUND, INC., Glendale, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/015,533

(22) Filed: Jan. 9, 2025

(65) Prior Publication Data

US 2025/0143634 A1 May 8, 2025

Related U.S. Application Data

(63) Continuation of application No. 18/617,398, filed on Mar. 26, 2024, now Pat. No. 12,220,245, which is a
(Continued)

(51) Int. Cl.
*A61B 5/00* (2006.01)
*A61B 8/00* (2006.01)

(52) U.S. Cl.
CPC .............. *A61B 5/4519* (2013.01); *A61B 8/48* (2013.01); *A61B 8/5215* (2013.01); *A61B 8/5223* (2013.01)

(58) Field of Classification Search
CPC ....... A61B 5/4519; A61B 8/48; A61B 8/5215; A61B 8/5223; G16H 50/20; G16H 50/30
See application file for complete search history.

(56) References Cited

U.S. PATENT DOCUMENTS 4,831,527 A 5/1989 Clark
4,876,733 A 10/1989 Lavin
(Continued)

FOREIGN PATENT DOCUMENTS

KR 20130006011 1/2013
WO WO 14/115056 7/2014

OTHER PUBLICATIONS

Costill et al., "Muscle glycogen utilization during prolonged exercise on successive days," Journal of Applied Physiology, 1971, vol. 31, No. 6, pp. 834-838.
(Continued)

*Primary Examiner* — Sanjay Cattungal
(74) *Attorney, Agent, or Firm* — Brownstein Hyatt Farber Schreck, LLP

(57) ABSTRACT

Provided is a non-invasive system and method for determining a fuel value for a target muscle and potentially at least one indicator muscle. The method includes receiving an ultrasound scan of a target muscle; evaluating at least a portion of the ultrasound scan to determine fuel value within the target muscle; recording the determined fuel value for the muscle as an element of a data set for the muscle; evaluating the fuel data set to determine a value range; and in response to the range being at least above a pre-determined threshold, establishing a target score for the muscle as based on an upper portion of the value range. The method may be repeated to identify ranges for a plurality of muscles, the muscle with the greatest range being identified as an
(Continued)

indicator muscle. Based thereon, the muscles estimated fuel level, fuel rating and energy status may be determined.

20 Claims, 32 Drawing Sheets

Related U.S. Application Data continuation of application No. 18/103,995, filed on Jan. 31, 2023, now Pat. No. 12,004,866, which is a continuation of application No. 17/410,378, filed on Aug. 24, 2021, now Pat. No. 11,602,304, which is a continuation of application No. 15/909,593, filed on Mar. 1, 2018, now Pat. No. 11,160,493.

(60) Provisional application No. 62/466,844, filed on Mar. 3, 2017.

(56)                   References Cited

U.S. PATENT DOCUMENTS

| 5,208,747 | A | 5/1993 | Wilson et al. |
| 5,670,135 | A | 9/1997 | Schroder |
| 5,941,825 | A | 8/1999 | Lang et al. |
| 6,542,250 | B1 | 4/2003 | Michaelis et al. |
| 6,656,121 | B2 | 12/2003 | Jeong et al. |
| 6,705,994 | B2 | 3/2004 | Vortman et al. |
| 6,891,961 | B2 | 5/2005 | Eger et al. |
| 7,658,714 | B2 | 2/2010 | Leibig et al. |
| 7,664,298 | B2 | 2/2010 | Lang et al. |
| 7,683,617 | B2 | 3/2010 | Van Zijl et al. |
| 7,809,153 | B2 | 10/2010 | Bravomalo |
| 7,918,794 | B2 | 4/2011 | Pineau et al. |
| 8,068,899 | B2 | 11/2011 | Llewellyn et al. |
| 8,135,179 | B2 | 3/2012 | Wilson et al. |
| 8,351,655 | B2 | 1/2013 | Hwang |
| 8,512,247 | B2 | 8/2013 | Hill |
| 8,517,942 | B2 | 8/2013 | Hill |
| 8,562,529 | B2 | 10/2013 | Hill |
| 8,715,187 | B2 | 5/2014 | Davis et al. |
| 8,811,745 | B2 | 8/2014 | Farsiu et al. |
| 9,364,179 | B2 | 6/2016 | Hill |
| 9,497,976 | B2 * | 11/2016 | Sun .......................... A23L 25/00 |
| 9,555,052 | B2 * | 1/2017 | Paturu ................... A61M 39/04 |
| 9,579,079 | B2 | 2/2017 | Jeanne et al. |
| 9,642,593 | B2 * | 5/2017 | Sarnow ................ A61B 5/4872 |
| 9,873,868 | B2 * | 1/2018 | Koeberl .................... A61P 3/00 |
| 9,996,926 | B2 | 6/2018 | Leinhard et al. |
| 10,028,700 | B2 | 7/2018 | Sarnow et al. |
| 10,157,465 | B2 | 12/2018 | Sugiyama et al. |
| 10,327,692 | B2 | 6/2019 | Uchiyama |
| 10,463,346 | B2 * | 11/2019 | Hill .......................... A61B 8/08 |
| 10,548,528 | B2 | 2/2020 | Appleby |
| 11,013,490 | B2 | 5/2021 | Sarnow et al. |
| 11,064,971 | B2 | 7/2021 | Sarnow et al. |
| 11,096,658 | B2 | 8/2021 | Sarnow et al. |
| 11,121,176 | B2 * | 9/2021 | Liu ....................... H10N 70/021 |
| 11,147,481 | B1 * | 10/2021 | Kirby ................ A61B 5/14546 |
| 11,160,493 | B2 * | 11/2021 | Sarnow ................... G16H 50/30 |
| 11,229,787 | B2 * | 1/2022 | Daniels .................. H01B 13/00 |
| 11,261,460 | B2 * | 3/2022 | Byrne ...................... C12N 7/00 |
| 11,389,372 | B2 * | 7/2022 | Warlick ............... A61H 23/008 |
| 11,389,373 | B2 * | 7/2022 | Warlick ............... G10K 15/043 |
| 11,602,304 | B2 | 3/2023 | Sarnow et al. |
| 11,612,376 | B2 | 3/2023 | Sarnow et al. |
| 11,623,043 | B2 * | 4/2023 | Lipschultz ............. G16H 50/20 |
| | | | 600/427 |
| 11,627,934 | B2 | 4/2023 | Sarnow et al. |
| 11,813,111 | B2 | 11/2023 | Sarnow et al. |
| 11,911,003 | B2 * | 2/2024 | McDowall ......... A61B 1/00186 |
| 12,004,866 | B2 | 6/2024 | Sarnow et al. |
| 2003/0018257 | A1 | 1/2003 | Hsu et al. |
| 2006/0184024 | A1 | 8/2006 | Da Silva et al. |
| 2007/0016061 | A1 | 1/2007 | Da Silva et al. |
| 2009/0264756 | A1 | 10/2009 | Da Silva et al. |
| 2009/0270728 | A1 | 10/2009 | Da Silva et al. |
| 2010/0036246 | A1 | 2/2010 | Kushculey et al. |
| 2012/0116223 | A1 | 5/2012 | Da Silva et al. |
| 2012/0165703 | A1 | 6/2012 | Bottum |
| 2012/0254749 | A1 | 10/2012 | Downs, III et al. |
| 2013/0123629 | A1 | 5/2013 | Rosenberg et al. |
| 2015/0374343 | A1 | 12/2015 | Shan et al. |
| 2021/0321979 | A1 | 10/2021 | Sarnow et al. |
| 2024/0041425 | A1 | 2/2024 | Sarnow et al. |
| 2024/0237939 | A1 | 7/2024 | Sarnow et al. |

OTHER PUBLICATIONS

Definition of "doubling," https://www.thefreedictionary.com/doubling, retrieved on Jan. 28, 2021.

Definition of "Sleek," https://https://www.merriam-webster.com/dictionary/sleek, retrieved on Aug. 2022.

Elamaran et al., "A Case Study of Impulse Noise Reduction Using Morphological Image Processing with Structuring Elements," Asian Journal of Scientific Research, vol. 8, No. 3, 2015, pp. 291-303.

Fisher et al., "Spatial Filters—Gaussian Smoothing," https://homepages.inf.ed.ac.uk/rbf/HIPR2/gsmooth.htm, Apr. 24, 2020, 9 pages.

Gabriel et al., "Ultrasound of the abdomen in endurance athletes," Eur J Appl Physiol, 1996, vol. 73, pp. 191-193.

Hendrick et al., "Image and Signal Processing in Diagnotic Ultrasound Imaging" JDMS 1989 5:231-239.

Jackson et al., "Practical Assessment of Body Composition," Physicians Sports Medicine, 1985, vol. 13, pp. 76-90.

Kadah et al., "Classification Algorithms for Quantitative Tissue Characterization of Diffuse Liver Disease from Ultrasound Images," IEEE Transactions on Medical Imaging, 1996, vol. 15, No. 4, pp. 466-478.

Kawakami, Y. et al. "Muscle-fiber pennation angles are greater in hypertrophied than in normal muscles" (1993) J. Appl. Physiol. 74(6) 2740-2744.

Koda et al., "Sonographic subcutaneous and visceral fat indices represent the distribution of body fat volume," Abdominal Imaging, 2007, vol. 32, pp. 387-392.

Leahy et al., "Ultrasound Measurement of Subcutaneous Adipose Tissue Thickness Accurately Predicts Total and Segmental Body Fat of Young Adults," Ultrasound in Medicine and Biology, 2012, vol. 38, No. 1, pp. 28-34.

MathWorks Announces Release 2014a of the MATLAB and Simulink Product Families, https://www.mathworks.com/company/newsroom/mathworks-announces-release-2014a-of-the-matlab-and-simulink-product-families.html, Mar. 7, 2014, 6 pages.

Nguyen et al., "Contrast-Enhanced Ultrasonography in Patients with Glycogen Storage Disease Type Ia and Adenomas," Journal of Ultrasound Medicine, 2009, vol. 28, pp. 497-505.

Price et al., "Effect of muscle glycogen content on exercise-induced changes in muscle T2 times," Muscle Glycogen, Exercise, and T2 Times, 1998, pp. 1178-1184.

Ramsey, J. et al. "Differences in Plantar Flexor Fascicle Length and Pennation Angle Between Healthy and Poststroke Individuals and Implications for Poststroke Plantar Flexor Force Contributions" (2014) Stroke Research and Treatment vol. 2014 6 pages.

Salvi, "Architectural Analysis of Musculoskeletal Ultrasound Images," Politecnico di Torino, Dec. 2014, 61 pages.

Steensberg et al., "Muscle glycogen content and glucose uptake during exercise in humans: influence of prior exercise and dietary manipulation," Journal of Physiology, vol. 541.1, 2002, pp. 273-281.

The University of Auckland, "Gaussian Filtering," May 25, 2010, 15 pages.

Wagner, "Ultrasound as a Tool to Assess Body Fat," Journal of Obesity, vol. 2013, Article ID 280713, 9 pages.

Zhou et al., "Automatic measurement of pennation angle and fascicle length of gastrocnemius muscles ultrasound imaging," Ultrasonics, vol. 57, 2015, pp. 72-83.

(56)               References Cited

OTHER PUBLICATIONS

Zhou et al., "Dynamic measurement of pennation angle of gastroc-nemius muscles during contractions based on ultrasound imaging" (2012) 11:63 10 pages.

Zhu, S. et al., "The correlation of muscle thickness and pennation angle assessed by ultrasound with sarcopenia in elderly Chinese community dwellers"(2019) Clinical Interventions in Aging 14:987-996.

\* cited by examiner

FIG. 5
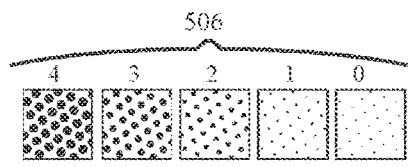
Fuel Concentration
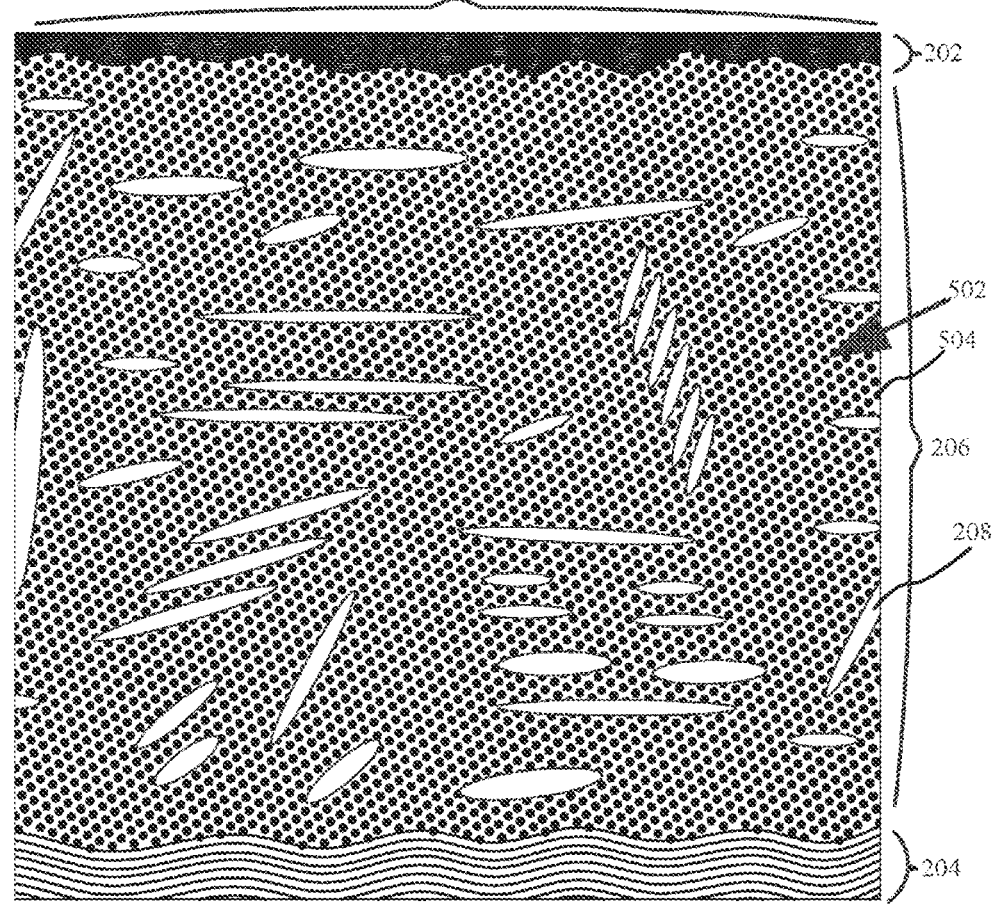

Average
3.38

Refined Evaluation
3.90

| A | B | C | D | E | F | G | H | I | J | K | L |  |
|---|---|---|---|---|---|---|---|---|---|---|---|---|
|   |   |   |   |   |   |   |   |   |   |   |   | 1 |
| 3 | 2 | 3 | 3 | 3 | 3 | 3 | 4 | 3 | 4 |   |   | 2 |
| 3 | 2 | 3 | 3 | 2 | 3 | 3 | 2 | 2 | 3 |   |   | 3 |
| 3 | 2 | 3 | 2 | 2 | 3 | 3 | 3 | 3 | 3 |   |   | 4 |
| 3 | 3 | 2 | 2 | 3 | 3 | 3 | 3 | 2 | 3 |   |   | 5 |
| 3 | 2 | 3 | 3 | 2 | 3 | 2 | 3 | 3 | 3 |   |   | 6 |
| 4 | 3 | 2 | 2 | 3 | 3 | 3 | 3 | 3 | 3 |   |   | 7 |
| 3 | 3 | 2 | 3 | 3 | 3 | 2 | 3 | 3 | 4 |   |   | 8 |
| 3 | 4 | 4 | 3 | 4 | 4 | 2 | 3 | 2 | 4 |   |   | 9 |
| 3 | 3 | 4 | 4 | 4 | 4 | 3 | 3 | 3 | 3 |   |   | 10 |
| 4 | 4 | 4 | 3 | 4 | 3 | 3 | 4 | 4 | 4 |   |   | 11 |
|   |   |   |   |   |   |   |   |   |   |   |   | 12 |

Average
2.99

| A | B | C | D | E | F | G | H | I | J | K | L | |
|---|---|---|---|---|---|---|---|---|---|---|---|---|
| | | | | | | | | | | | | 1 |
| | 3 | 2 | 3 | 3 | 2 | 2 | 2 | 2 | 2 | 3 | | 2 |
| | 2 | 2 | 2 | 2 | 1 | 2 | 2 | 2 | 2 | 3 | | 3 |
| | 2 | 2 | 1 | 1 | 1 | 1 | 2 | 2 | 1 | 3 | | 4 |
| | 2 | 1 | 1 | 1 | 1 | 1 | 2 | 2 | 1 | 2 | | 5 |
| | 2 | 2 | 2 | 1 | 2 | 2 | 2 | 1 | 1 | 1 | | 6 |
| | 1 | 2 | 1 | 1 | 1 | 1 | 1 | 1 | 2 | 2 | | 7 |
| | 2 | 1 | 1 | 1 | 2 | 1 | 2 | 1 | 2 | 2 | | 8 |
| | 2 | 2 | 2 | 1 | 2 | 1 | 1 | 1 | 1 | 2 | | 9 |
| | 3 | 1 | 1 | 2 | 2 | 2 | 1 | 1 | 2 | 3 | | 10 |
| | 4 | 2 | 3 | 2 | 3 | 3 | 3 | 2 | 2 | 4 | | 11 |
| | | | | | | | | | | | | 12 |

Average
1.8

| A | B | C | D | E | F | G | H | I | J | K | L | |
|---|---|---|---|---|---|---|---|---|---|---|---|---|
| | | | | | | | | | | | | 1 |
| | 1 | 0 | 1 | 1 | 0 | 1 | 1 | 1 | 1 | 1 | | 2 |
| | 0 | 0 | 0 | 0 | 0 | 0 | 0 | 0 | 0 | 0 | | 3 |
| | 0 | 0 | 0 | 0 | 0 | 0 | 0 | 0 | 0 | 0 | | 4 |
| | 0 | 0 | 0 | 0 | 0 | 0 | 0 | 0 | 0 | 0 | | 5 |
| | 0 | 0 | 0 | 0 | 0 | 0 | 0 | 0 | 0 | 0 | | 6 |
| | 1 | 0 | 0 | 0 | 0 | 0 | 0 | 0 | 0 | 0 | | 7 |
| | 1 | 0 | 0 | 1 | 1 | 1 | 0 | 1 | 0 | 0 | | 8 |
| | 1 | 1 | 1 | 1 | 1 | 1 | 1 | 1 | 1 | 0 | | 9 |
| | 1 | 0 | 1 | 2 | 2 | 2 | 1 | 1 | 1 | 1 | | 10 |
| | 2 | 2 | 2 | 2 | 2 | 3 | 1 | 1 | 2 | 2 | | 11 |
| | | | | | | | | | | | | 12 |

Average
0.54

FIG. 11

FIG. 14
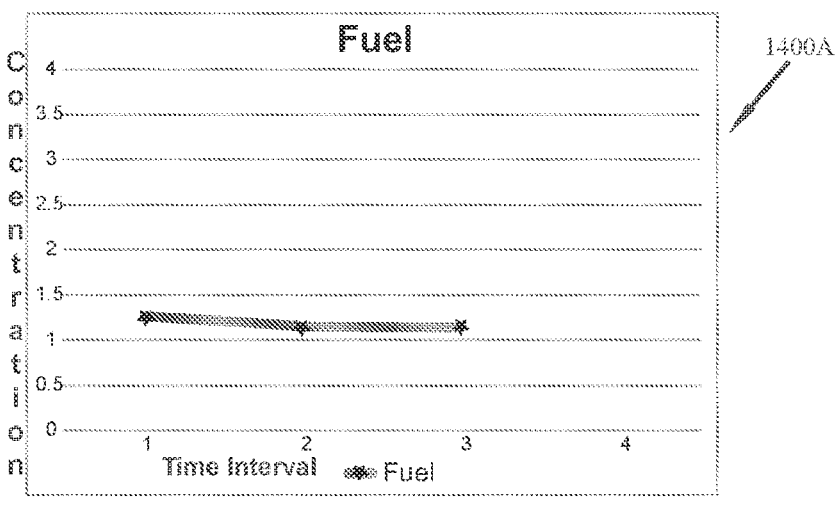
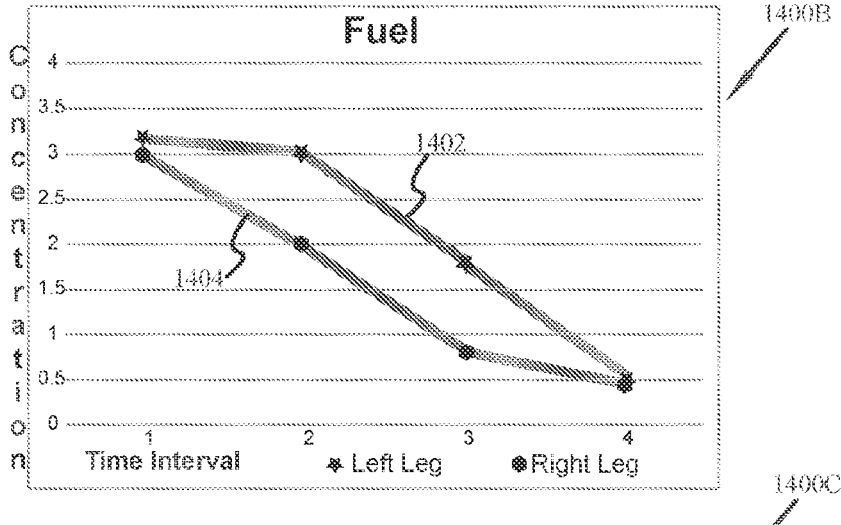
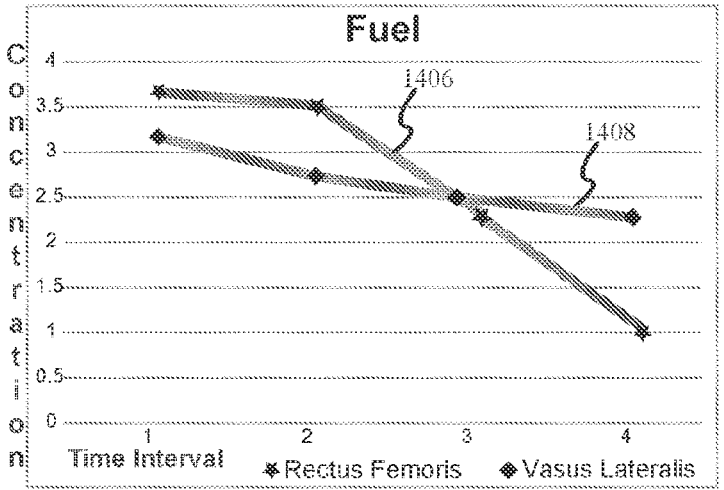

Figure 15:
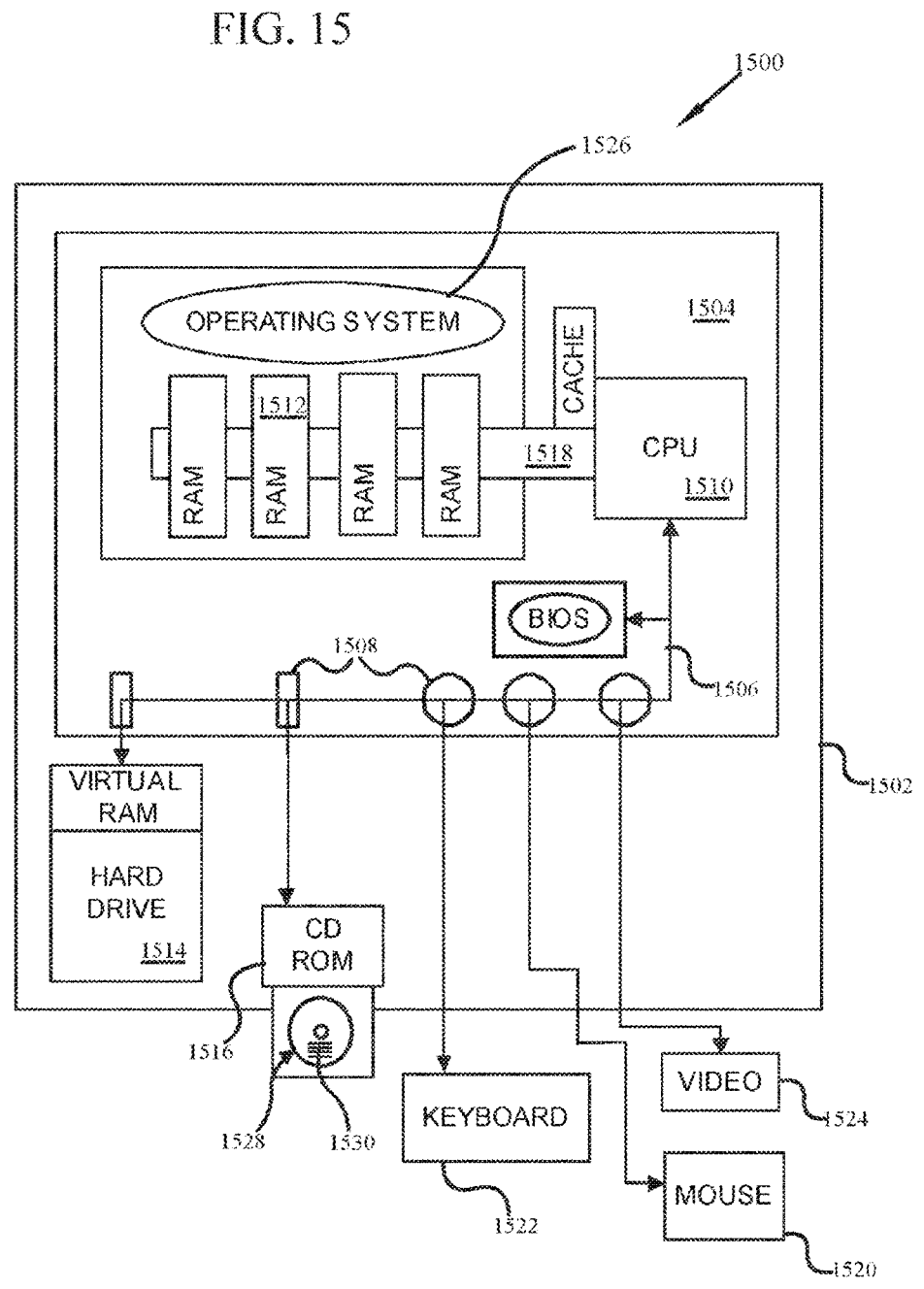

OPERATING SYSTEM

CACHE

1512

RAM

RAM

RAM

RAM

1518

CPU

1510

BIOS

1508

1506

1502

VIRTUAL RAM

HARD DRIVE

1514

CD ROM

1516

1528 1530

KEYBOARD

1522

VIDEO

1524

MOUSE

1520

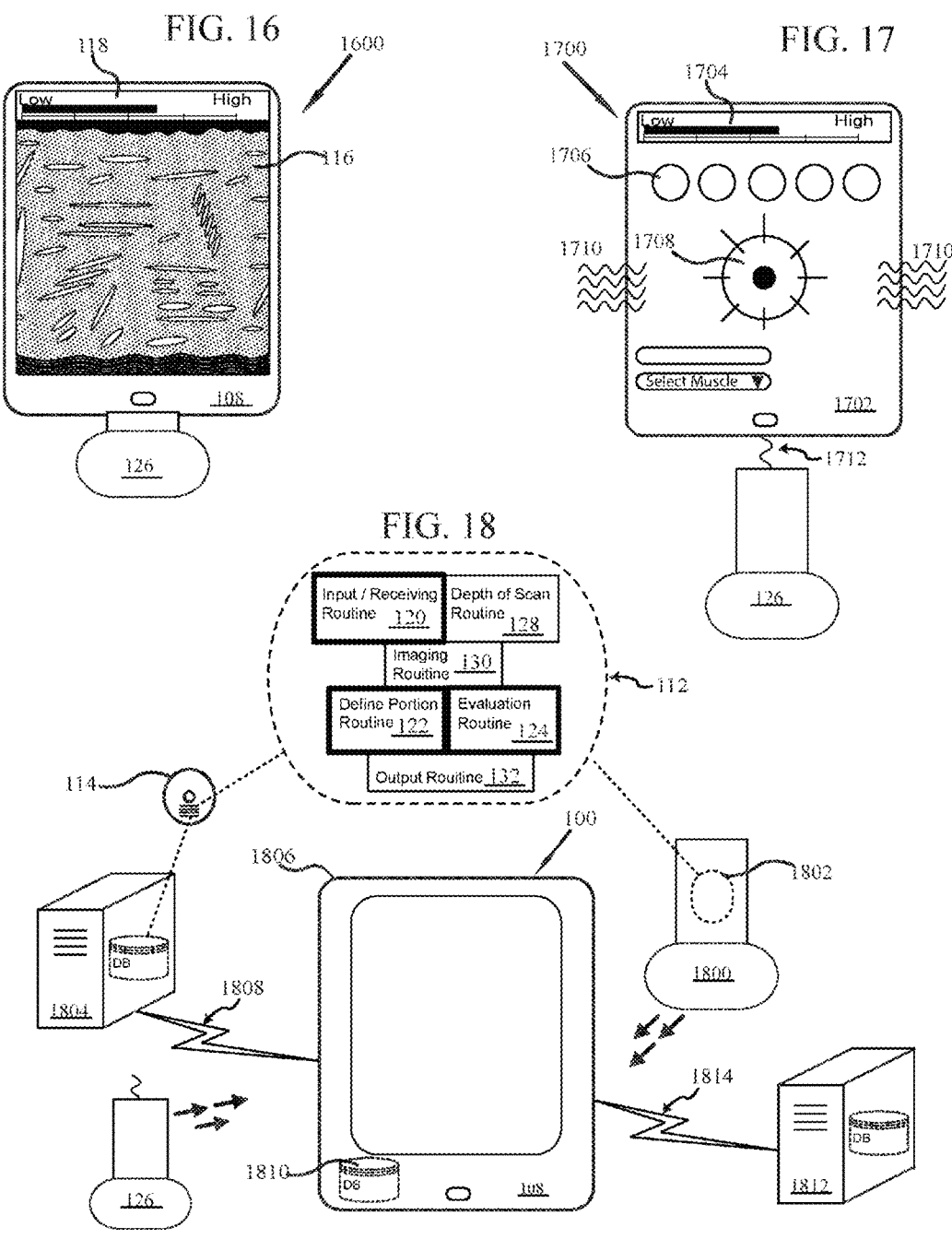

2200

50%

25%                    75%

0%                                      100%

2202

SYSTEM AND METHOD FOR DETERMINING A SUBJECT'S MUSCLE FUEL LEVEL, MUSCLE FUEL RATING, AND MUSCLE ENERGY STATUS

CROSS-REFERENCE TO RELATED APPLICATION

This application is a continuation of U.S. patent application Ser. No. 18/617,398, filed Mar. 26, 2024, and titled "System and Method for Determining a Subject's Muscle Fuel Level, Muscle Fuel Rating, and Muscle Energy Status" which is a continuation of U.S. patent application Ser. No. 18/103,995, filed Jan. 31, 2023, and titled "System and Method for Determining a Subject's Muscle Fuel Level, Muscle Fuel Rating, and Muscle Energy Status" U.S. Pat. No. 12,004,866, which is a continuation of U.S. patent application Ser. No. 17/410,378, filed Aug. 24, 2021, and titled "System and Method for Determining a Subject's Muscle Fuel Level, Muscle Fuel Rating, and Muscle Energy Status", now U.S. Pat. No. 11,602,304 which is a continuation of U.S. patent application Ser. No. 15/909,593, filed Mar. 1, 2018, and titled "System and Method for Determining a Subject's Muscle Fuel Level, Muscle Fuel Rating, and Muscle Energy Status," now U.S. Pat. No. 11,160,493, which claims the benefit under 35 U.S.C. § 119 (e) of U.S. Provisional Patent Application No. 62/466,844, filed Mar. 3, 2017, and titled "System and Method for Muscle Energy Status Determination and Evaluation," the contents of which are incorporated by reference as if fully disclosed herein.

FIELD

The present invention relates generally to the determination of muscle fuel in animal and human tissue, and more specifically to the non-invasive determination of a muscle fuel level, muscle fuel rating, and overall muscle energy status in animal and human tissue.

BACKGROUND

Skeletal muscle makes up approximately 40% of ones total body mass. The health of your skeletal muscles makes an essential contribution to your wellbeing at any age and at any level of fitness or mobility. One indicator of a skeletal muscle's health is how much energy that muscle is storing at any given time.

Muscle's depend on energy for performance. A primary constituent for a muscle's energy is glycogen, as well as other energy constituents, e.g., protein, carnitine, and creatine. Glycogen is the storage form of glucose in animal and human tissues. Moreover it is the polysaccharide molecule that functions as the secondary long-term energy store in animal cell tissue and may be represented as $(C_6H_{10}O_5)_n$. Glycogen is made up of glucose building blocks, glucose $(C_6H_{12}O_6)$ being a monosaccharide, or simple sugar and an important carbohydrate in biology. Glycogen is made primarily by the liver and the muscles, but it can also be made by glycogenesis within the brain and stomach. Proteins, carnitine and creatine are each constituents involved in supporting healthy muscle performance, being involved in muscle metabolism, ATP production, and/or other energy involved processes. However, glycogen and other energy constituents have traditionally only been measured by a limited number of intrusive procedures, like biopsies, or estimates based on past performance parameters. These techniques have limited utility, and provide little guidance on a real time scale.

Hence there is a need for a method and system that is capable of providing non-intrusive determinations for how much energy a muscle is storing, particularly methods and systems that can be performed at real time.

SUMMARY

This invention provides methods and systems for the non-invasive determination of fuel, fuel level, fuel rating and energy status for a muscle and, therefore, for the overall performance readiness of a muscle.

In particular, and by way of example only, according to one embodiment of the present invention, provided is a non-invasive method of determining at least one indicator muscle for determination of muscle fuel, comprising: receiving from a subject a plurality of ultrasound scans from a plurality of different muscles over a plurality of ultrasound scanning sessions; for each received ultrasound scan of each muscle, evaluating at least a portion of the ultrasound scan to determine a fuel value within the muscle, the collective fuel values being a data set for the muscle; evaluating each fuel data set to determine a range for each muscle; ranking the scanned muscles by determined range; and selecting at least the highest ranked muscle as at least one indicator muscle.

In one embodiment, provided is a non-invasive method of determining a target fuel level for a target or indicator muscle, comprising: receiving from a subject a plurality of ultrasound scans of the target muscle over a plurality of ultrasound scanning sessions; for each received ultrasound scan, evaluating at least a portion of the ultrasound scan to determine fuel values within the muscle, the collective fuel values being a fuel value data set for the muscle; evaluating the data set to determine a value range and assigning a maximum fuel value as 100 and a minimum fuel value as 1; evaluating a new real time ultrasound scan and determining the fuel value, such that the new fuel value is placed within the 100 to 1 fuel value range; and assigning a fuel level for the muscle. In aspects of the above embodiment, the fuel level is provided as a percentage and likened to a fuel tank.

In another embodiment, the target or indicator muscle's fuel level is compared to a fuel level data set for the same muscle in other individuals. The comparison provides a fuel rating (or how does the target muscle compare to others who have been tested in the same way) for the target muscle. In some aspects, the other individuals are the same gender as the subject, are the same age as the subject, or compete in the same athletic endeavors as the subject.

In still another embodiment, the target or indicator muscle's fuel level and fuel rating are combined to provide a composite score. The composite score is indicative of a muscle energy status for the target muscle, or a muscle readiness for the target muscle. As for muscle ratings, muscle energy status can be compared to other individuals, and can be defined as a numeric score (1-100) or a status score (low, average, high).

In some aspects, the fuel level, fuel rating or energy status for a target muscle can be compared against the same score established for its contralateral muscle to provide a muscle fuel symmetry. Target muscles that are non-symmetric with regard to muscle fuel level, muscle rating or energy status are at a higher risk of injury.

BRIEF DESCRIPTION OF THE DRAWINGS

At least one method and system for non-invasive determination of glycogen stores will be described, by way of example in the detailed description below with particular reference to the accompanying drawings in which like numerals refer to like elements, and:

FIG. 5 is a conceptual illustration of an ultrasound scan of a target muscle at a first time interval in accordance with at least one embodiment;

FIG. 11 is a conceptual illustration of an ultrasound scan of a target muscle further showing a user adjusted/determined selection of an area for evaluation in accordance with at least one embodiment;

FIG. 14 presents multiple charts illustrating the fatigue and the comparison of different target muscles in accordance with at least one embodiment;

FIG. 15 is a block diagram of a computer system in accordance with at least one embodiment; and FIGS. 16-18 are conceptual illustrations of alternative configurations for a system for non-invasive determination of fuel values in accordance with at least one embodiment;

DETAILED DESCRIPTION

Before proceeding with the detailed description, it is to be appreciated that the present teaching is by way of example only, not by limitation. The concepts herein are not limited to use or application with a specific system or method for non-invasive determination of a muscle's fuel. Thus although the instrumentalities described herein are for the convenience of explanation shown and described with respect to exemplary embodiments, it will be understood and appreciated that the principles herein may be applied equally in other types of systems and methods involving in the non-invasive determination of fuel, fuel levels, fuel rating, fuel symmetry and energy for a muscle.

Glycogen is a polysaccharide made up of glucose—a monosaccharide, or simple sugar and an important carbohydrate in biology. Indeed glycogen is a principle form of energy storage for an animal and therefore referred to as a "glycogen store." Carnitine is a compound found in the muscle involved in the transfer of fatty acids across mitochondrial membranes. Creatine is a protein involved in energy supply in the muscle and involved in muscle contraction. Other water soluble proteins and energy constituents are also found in muscle that are useful in building and repairing muscle. The combination of glycogen, carnitine, creatine and other proteins is referred to as fuel or muscle fuel herein. For ease of discussion and illustration, the embodiments of systems and methods as set forth herein discuss and describe non-invasive determination of fuel, where fuel may include any useful monosaccharide, polysaccharide, protein, compound and the like useful in providing energy to a muscle. Each of these fuel constituents improves endurance of a muscle and delays fatigue, and depletion of a muscle's fuel is indicative of whether a muscle is ready for exercise and possible prone to injury. Each of these constituents is water-bound and enters the muscle tightly associated with water.

Figure 1:
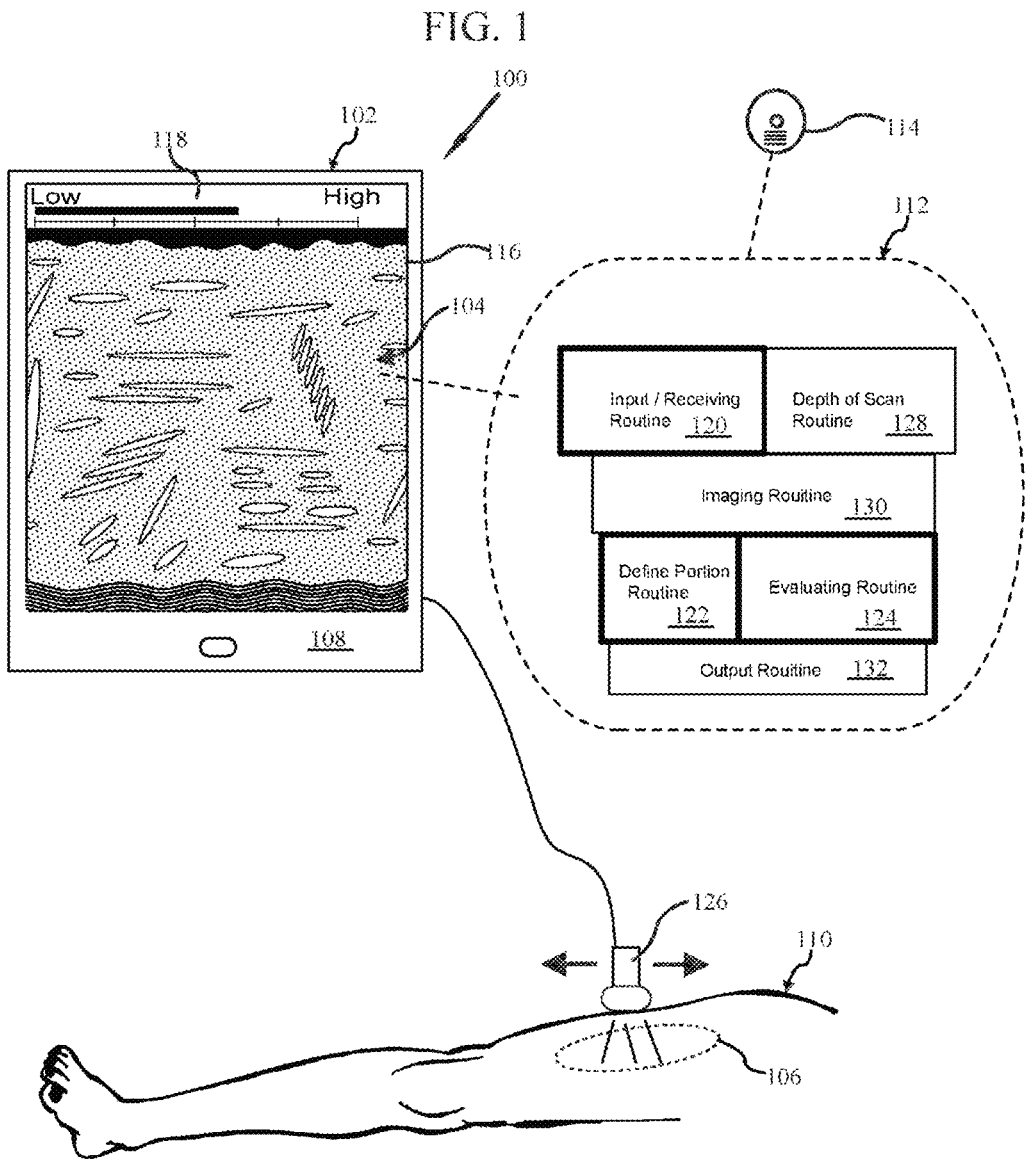
FIG. 1 illustrates a high level block diagram of a system for non-invasive determination of fuel in accordance with at least one embodiment.

Turning to FIG. 1, presented is a high level block diagram of a system for non-invasive determination of muscle fuel (SNDGS) 100. Specifically, SNDS 100 is a fuel evaluator 102 structured and arranged to evaluate at least one selected portion of a scan 104 of a selected target muscle 106 to determine fuel within the target muscle 106.

As used herein the term "scan" is understood and appreciated for its normal meaning and as is expected in the medical profession—namely, "a. examination of the body or an organ or part, or a biologically active material, by means of a scanning technique such as ultrasonography—an ultrasound-based diagnostic imaging technique used for visualizing subcutaneous body structures b. the image so obtained. Moreover the scan may be the collection of data from a scanner as well as an image representing that data, but it need not be an image in all cases.

Further the term "evaluate" and its various derivatives is understood and appreciated for its normal meaning, namely, "a. to determine or set the value or amount of; appraise—b. to judge or determine the significance, worth or quality of, assess—c. to ascertain the numerical value of" However, with respect to the interpretation of scans, it is not uncommon to refer to the process of interpretation as analyzing, as in, "a. to separate into constituent parts or elements; determine the elements or essential features of—b. to examine critically, so as to bring out the essential elements or give the essence of—c. to examine carefully and in detail so as to identify causes, key factors, possible results, etc. . . . —d. to subject to mathematical, chemical, grammatical, etc., analysis." Moreover, as used herein, "evaluate" and it's derivative forms are understood and appreciated to encompass the aspects of "analysis" as may be appropriate for a given situation.

In at least one embodiment, SNDGS 100 has a processor-enabled device such as computer 108. Computer 108 is adapted to receive the scan 104 of a target muscle 106 of a subject 110, FIG. 1 showing only a portion of the subject's right leg.

With respect to FIG. 1, the conceptual illustration suggests the subject 110 is a human being. Indeed, embodiments of SNDGS 100 are indeed directed towards the non-invasive detection and analysis of fuel within human beings, such as for example, elite athletes such as professional cyclists, triathletes, speed skaters, swimmers, downhill and slalom skiers, football players, lacrosse players, soccer players, and or other such endurance athletes or individuals such as military personnel, where sustained performance over an extended period of time is a significant factor in the person's training and conditioning. It should also be understood that varying embodiments of SNDGS 100 might also be applied to non-human subjects, such as racehorses or other animals.

With respect to FIG. 1, SNDGS 100 is at least in part conceptually illustrated in the context of an embodiment for a computer program 112. Such a computer program 112 can be provided upon a non-transitory computer readable media, such as an optical disc 114 or RAM drive that can be provided to a computer 108 to be adapted as SNDGS 100. As is further shown and described in connection with FIG. 16, in alternative embodiments the computer program 112 can be provided to a computer serving at least as part of an application providing platform, such as but not limited to the Apple App Store, that computer in turn operable to provide the computer program to a computer 108 to be adapted as SNDGS 100.

As will be discussed further below, SNDGS 100 may be employed upon a computer 108 having typical components such as a processor, memory, storage devices and input and output devices. During operation, the SNDGS 100 may be maintained in active memory for enhanced speed and efficiency. In addition, SNDGS 100 may also be operated within a computer network and may utilize distributed resources.

In at least one embodiment, the SNDGS 100 system is provided as a dedicated system to provide non-invasive determination of muscle fuel. In at least one alternative embodiment, the SNDGS 100 system is achieved by adapting an existing computer 108 such as a smart phone (such as an iPhone® or Android®) or tablet computer (such as an iPad®) which is portable.

With respect to FIG. 1, SNDGS 100 has been conceptually illustrated as a tablet computer 108, having a display 116 operable to display a visual representation of the scan 104. The display 116 also is shown to provide an indicator 118 to inform an operator of the determined fuel level.

For at least one embodiment, the software may be described as including an input/receiving routine 120, a define portion routine 122, and an evaluating routine 124. As is set forth and described below, the elements of SNDGS 100 may be summarized or at least one embodiment as follows.

The input/receiving routine 120 is operable to receive the scan 104, such as a Digital Imaging and Communications in Medicine (DICOM) data file, and may also receive other information such as the subjects name, location, current state of exertion, etc. . . . . The define portion routine 122 is operable to define a plurality of areas within the scan 104 of the target muscle 106. The evaluating routine 124 is operable to evaluate at least one attribute for each of the plurality of areas to determine the fuel within the target muscle.

In addition to the three core routines, input/receiving routine 120, define area routine 122 and the evaluating routine 124 shown with heavy boarders, in at least one alternative embodiment, SNDGS 100 further includes an ultrasound device having a movable transducer 126 operable in a high frequency range and has a an adjustable depth of scan. More specifically, the high frequency range is between about 5 to 20 megahertz. In addition the depth of scan is between about 1 centimeter and about 7 centimeters. For at least one embodiment, the ultrasound transducer 126 is an existing commercially available and FDA approved ultrasound transducer 126 incorporated as part of SNDGS 100 without departing from the scope of FDA approval for the operation of the ultrasound transducer device.

For at least one embodiment of SNDGS 100, the computer program 112 may additionally include a depth of scan routine 128, an imaging routine 130, and optionally an output routine 132. Moreover, the depth of scan selector routine 128 is operable to adjust the ultrasound device, e.g., ultrasound transducer 126, for a depth of scan appropriate for the target muscle 106. In at least one embodiment, the proper depth of scan is set based on the selection of a target 106 muscle as indicated by an operator of SNDGS 100.

The imaging routine 130 is operable to direct the movable transducer 126 to scan the selected target muscle 106 by processing ultrasound reflection received by the transducer to provide at least a partial ultrasound scan of the selected target muscle. In at least one embodiment, the imaging routine 130 is structured and arranged to operate with a third party ultrasound imaging software provided to the computer 108.

For at least one embodiment, the optional output routine 132 is operable to output the scan of the target muscle 106 to a storage device, or database. This output routine may also be configured to provide an audible, visual or tactile output to inform the operator of SNGDS 100 of the determined fuel level for the target muscle 106.

With respect to FIG. 1, it is understood and appreciated that the elements, e.g., input routine 120, define area routine 122, evaluating routine 124, depth of scan routine 128, imaging routine 130, output routine 132, ultrasound transducer 126 and computer 108 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 2:
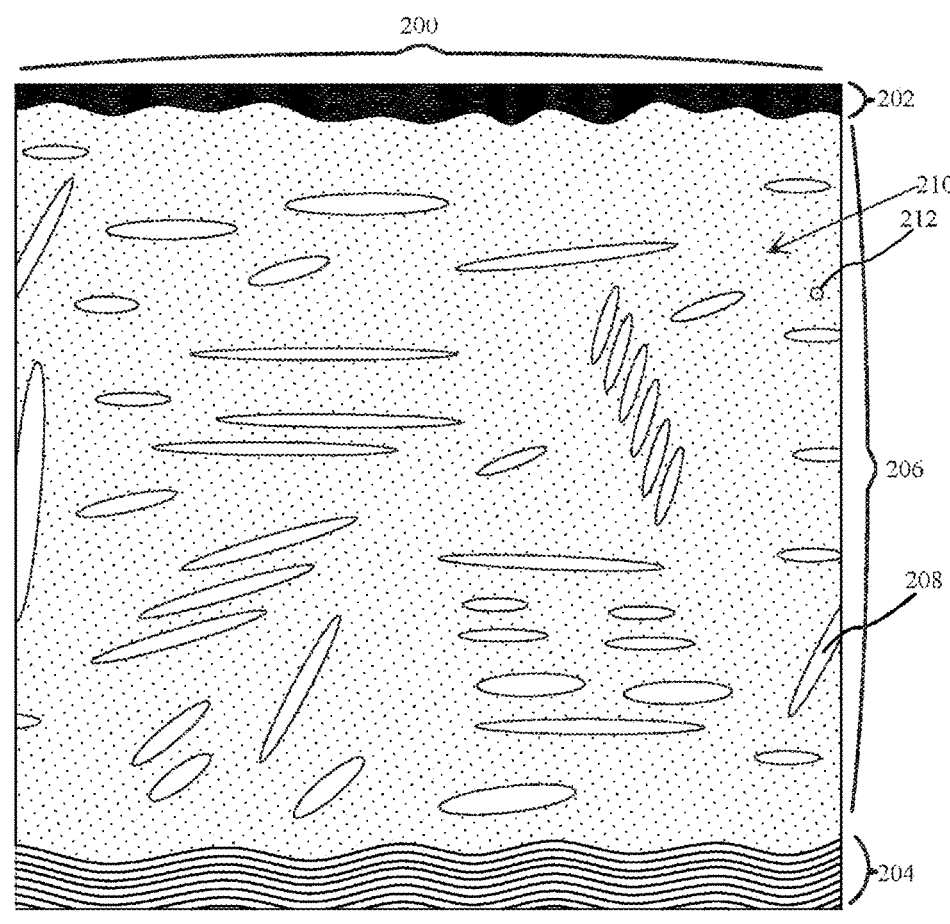
FIG. 2 is a conceptual illustration of an ultrasound scan of a target muscle in accordance with at least one embodiment.
Figure 3:
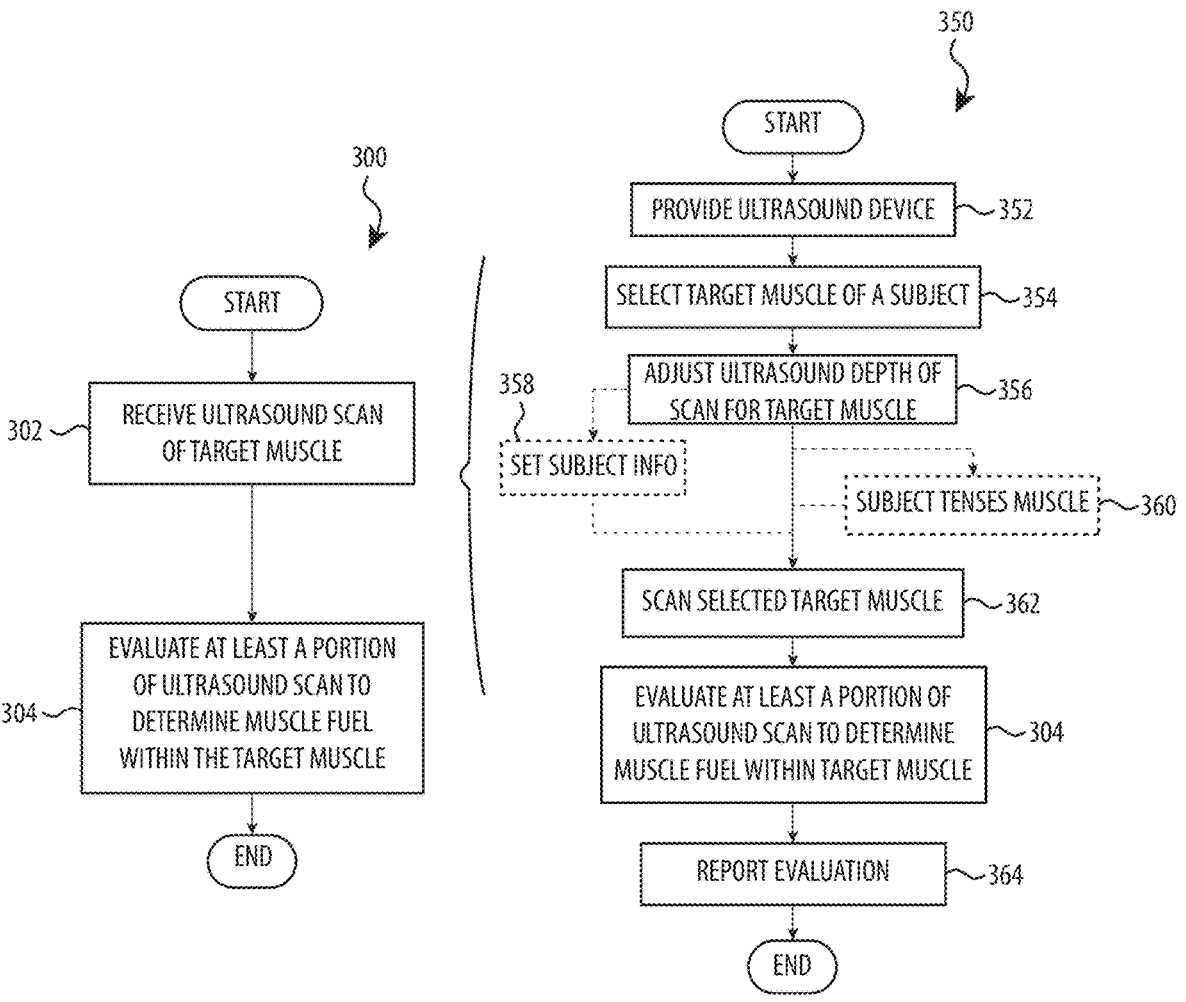
FIG. 3 illustrates a high level flow diagram for a method of non-invasive determination of fuel in accordance with at least one embodiment.

FIGS. 2 and 3 in connection with FIGS. 1 and 3-13 provide a high level flow diagram with conceptual illustrations depicting a method 300 for non-invasive determination of fuel in accordance with at least one embodiment. It will be appreciated that the described method need not be performed in the order in which it is herein described, but that this description is merely exemplary of one method of non-invasive determination of muscle fuel.

As is shown in FIG. 2, the scan 200 may capture a portion of the surface tissue 202, such as the skin and underlying fat and tissue layers. The scan 200 may also capture a portion of the deep tissue 206, bone, tendon, organ, or other tissue that is below the target muscle 106. Primarily, the scan 200 captures at least a portion of the target muscle 106, more specifically the target muscle tissue 206. Running throughout the muscle tissue 206 are various non-muscle tissues 208, such as but not limited to connective tissues, tendon tissues, and vascular tissues.

As the scan 200 presents at least a cross section of the muscle tissue 206, it is understood and appreciated that non-muscle tissue 208 that is truly within, connected to, or in contact with the muscle tissue 206 may appear as part of, or otherwise within the muscle tissue 206. For the purposes of non-invasive fuel determination as set forth herein, non-muscle tissues 208 that appear within the scan 200 of the muscle tissue 206 may be considered to be part of the muscle tissue 206.

Fuel 210 within the muscle tissue 206 are shown in FIG. 2 and in the accompanying figures as dots, with dot 212 being exemplary. For conceptual illustration and ease of discussion, the larger the fuel amount 210 the larger the dot 212. It is to be understood and appreciated that muscle fuel 210 is naturally occurring within the muscle tissue 206. Moreover, the methods and systems disclosed herein for non-invasive determination of fuel 210 within a target muscle 106 are advantageously distinct and directed to naturally occurring fuel 210, not injected glycogen, creatine, carnitine, and the like, as has been used to highlight internal structures and or features.

With respect to the development of fuel 210, carbohydrates are arguably the most important source of energy for animals, and more specifically mammals including human beings. Once eaten, carbohydrates are broken down into simple sugars such as glucose, fructose and galactose that are absorbed by cells and used for energy. Glucose that is absorbed by a muscle cell but not immediately needed is stored as glycogen, i.e., a component of the fuel 210. Muscle conditioning and training can increase the amount of muscle fuel 210. Whether through activity or simply the passage of time between eating, drinking and/or otherwise receiving carbohydrates, protein, creatine, etc., the fuel within muscles will be depleted. In addition, other constituents of fuel also increase in muscle based on healthy eating, conditioning and hydration, and are depleted by exercise and time. As such, muscle fuel is not a static parameter of muscle health, but rather a parameter that can be altered by how the muscle is treated.

With respect to the ultrasound scan 200, fuel can be detected as one or more attributes within the scan 200. More specifically, in many cases the scan 200 is rendered to a user of an ultrasound scanning system as an image. The attributes of the image correspond to sonogram reflection. More specifically, in at least one embodiment the scan 200 is represented as an image with attributes represented as luminance, color, contrast and or combinations thereof.

Further, although the accompanying FIGS. 1, and 2, 5-11 and 13 depict the scan 104 as an image, the interpretation of the scan 104 as an image has been chosen to facilitate ease of discussion and illustration. Indeed it is to be understood and appreciated that the varying embodiments of systems and methods for non-invasive fuel detection, attributes of the scan 104 may be interpreted without rendering an image to a user. Indeed, as is further discussed below other visual, audible or tactile notifications can be used to signify the determined fuel values with or without displaying an image of the scan to a user.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 3 in connection with FIG. 1 provides a high level flow diagram with conceptual illustrations depicting a method 300 for non-invasive determination of fuel within a target muscle 106. It will be appreciated that the described method, as well as all other subsequent methods and refinements to the disclosed methods need not be performed in the order in which they are herein described, but that the descriptions are merely exemplary of a method or methods that could be performed for non-invasive fuel determination.

More specifically, as in FIG. 3, for at least one embodiment, method 300 commences with receiving an ultrasound scan 104 of at least a portion of a target muscle 106, block 302. With the scan 104 received, at least a portion of the ultrasound scan 104 is evaluated to determine the fuel 210 within the target muscle 106, block 304.

For application of method 300, an embodiment of SNDGS 100 need not have, or otherwise be coupled to, an ultrasound transducer 126. Method 300 may also be performed by SNDGS 100 when a user desires to review historical data of target muscle scans, such as for example to revisit past histories of evaluation to perceive changes in development and potential adjustments to a subject's training methods. In addition, as discussed more fully below, historic data may be used to score a muscle's fuel level or even provide a rating for the muscle, which may also change over time.

Of course for real time and non-invasive determination of fuel, in varying embodiments SNDGS 100 may indeed include an ultrasound transducer 126 as described above. As such, method 300 may be augmented as method 350, the augmentation as illustrated pertaining to at least one method of providing the received ultrasound scan 104.

More specifically, for augmented method 350, an ultrasound transducer 126 is provided as part of SNDGS 100, block 352. A target muscle, e.g. target muscle 106, is selected, block 354. As noted, the ultrasound transducer has an adjustable depth for scanning, such as a selection between about 0.5 and 10 centimeters. The ultrasound transducer 126 is adjusted to provide a depth of scan appropriate for the selected target muscle, block 356.

In at least one embodiment, the depth of scan is adjusted manually, such as to about 3.5 centimeters for the rectus femoris muscle. In an alternative embodiment, the depth of scan is automatically selected by an operator selecting a muscle, e.g., rectus femoris, vastus lateralis, or biceps. In addition, in varying embodiment, the auto-determined and set depth may also be adjustable by the operator so as to permit adjustment for various body types.

In at least one embodiment additional and optional information about the subject is recorded, as indicated by dotted block 358. This optional information may include, but is not limited to, details such as the subjects name, age, gender, time of day, status of subject—at rest/at VO$_2$ Max, after eating, or other such information desired to be recorded and displayed in connection with the scanned image of the target muscle.

Moreover, to summarize for at least one embodiment, the augmented method 350 includes providing an ultrasound device having a movable transducer, the transducer operable in a high frequency range, selecting a target muscle 106 of a subject 110 and adjusting the ultrasound device for a depth of scan appropriate for the selected target muscle 106.

As the ultrasound transducer 126 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed the specific alignment as intended for the transducer should be used.

Testing has determined it is substantially immaterial as to whether the ultrasound transducer 126 is positioned along the longitudinal or latitudinal axis of the muscle, or somewhere there between. However for general alignment purposes and ease of operation, in general the operator of the system will select ultrasound transducer 126 alignment matching to either the longitudinal or latitudinal cross-sectional axis of the target muscle 106.

Application of the ultrasound transducer 126 against the subject's skin can be a practiced skill, for if too much pressure is applied the transducer may inadvertently compress the muscle tissue and thereby hamper the quality of the scan and the resulting evaluation of the fuel. However, an easy solution presents itself that substantially minimizes the risk of transducer related compression of the tissue.

As shown by optional dotted block 360, the subject can simply tense his or her target muscle 106. More specifically, if the subject acts to tense the selected target muscle 106, the natural action of the muscle contraction causes the muscle to swell and thereby resist compression. The contracted and thereby enlarged target muscle 106 may also be advantageous in providing an even clearer cross sectional scan then may be obtained with a relaxed muscle.

In short, while the quality of the scan for the tensed or un-tensed target muscle 106 may be the same for an operator skilled in how much pressure to apply, for the novice, as well as the skilled operator, tensing the target muscle 106 does not hamper the determination of fuel 210 and may help ensure greater consistency of scans in a wide variety of locations and settings. Indeed, for at least one embodiment, when the method of scanning a target muscle 106 is performed, the subject will tense his or her target muscle 106 as a normal and expected part of the scanning process.

Moreover, to achieve the scan of the target muscle 106, the ultrasound transducer 126 is disposed proximate to the target muscle and as the ultrasound transducer 126 is activated the target muscle 106 is scanned, block 362. In at least one embodiment the ultrasound transducer 126 is placed in direct contact with the subject's skin. In at least one alternative embodiment, a protective cover, shield or even the subject's clothing is disposed between the ultrasound transducer 126 and the target muscle 106.

In other words, to summarize for at least one embodiment, the augmented method 350 continues with disposing the transducer proximate to the subject 110 and perpendicular to the selected target muscle 106, and then imaging the selected target muscle 106 by processing ultrasound reflection received by the transducer to provide at least a partial scan of the selected target muscle 106. Many ultrasound transducers provide images as cross sections of the tissues and structures whereas others may provide 3-D views. For consistency in analysis, in at least one embodiment the operator of SNDGS 100 adopts a convention to scan a target muscle along its long axis or short axis. For the majority of leg and arm muscles the long axis is generally parallel to bone structure and the short axis is generally perpendicular to bone structure. Indeed in some embodiments, scans with SNDGS 100 may be performed substantially contemporaneously along both the long and short axis of a target muscle 106 for enhanced comparison and analysis.

Method 350 then continues with the evaluation of the scan as discussed above with respect to block 304. For at least one embodiment, it is understood and appreciated that the evaluation of the scan 104 is performed about contemporaneously with the scanning of the target muscle 106.

The determined fuel 210 is then reported to the operator, block 364. The determined fuel may also be recorded for use in plotting the changes in a subject's fuel level over time, and or in response to various different points of exercise and conditioning as well as different periods of exertion such as in endurance activities. As will be described in greater detail below, the determined fuel level may also be used to provide the subject with a fuel level, fuel rating, and energy status.

In at least one embodiment, the evaluation of the scan to determine the fuel value in the target muscle 106, is based on the visual experience of the operator performing the method 300, and or enhanced method 350 with respect to a visual image provided by the scan. More specifically an experienced individual can provide qualitative analysis of the fuel by visually determining an area of the cross section image to focus on and then evaluating that selected portion based on historical experience.

Methods 300/350 and or SNDGS 100 can advantageously be utilized by a greater audience of benefited parties where the evaluation is performed as an automated, or at least partially automated evaluation process.

Figure 4:
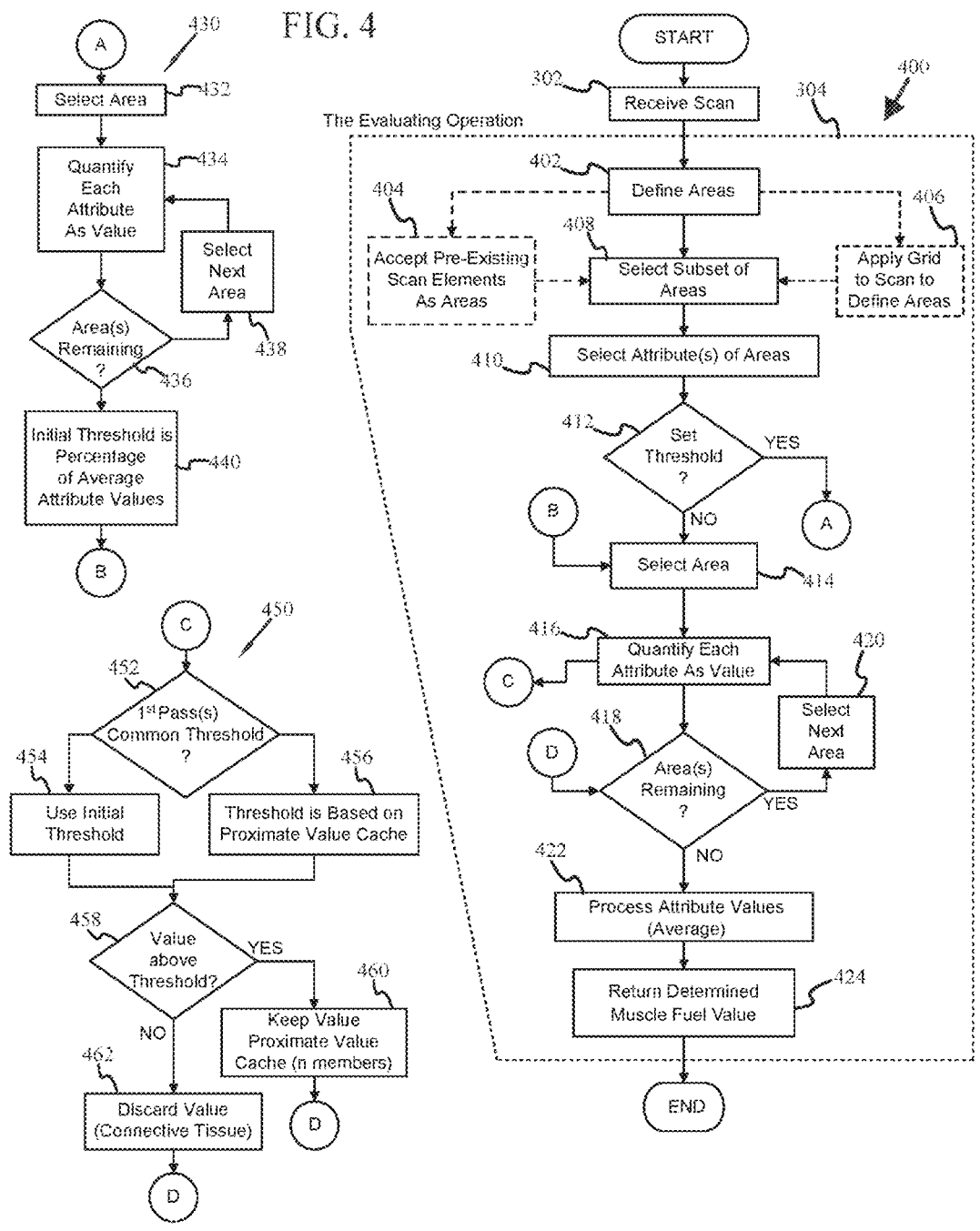
FIG. 4 is a refined flow diagram of the evaluating operation for non-invasive determination of fuel in accordance with at least one embodiment.

FIG. 4 in connection with FIGS. 5-13 provides a high level flow diagram with conceptual illustrations to further refine at least one embodiment of method 400 for evaluating at least a portion of the ultrasound scan to determine the fuel 210 within the target muscle 106. Again it is appreciated that the described method need not be performed in the order in which it is herein described, but that this description is merely exemplary of one method for non-invasive determination of fuel within a target muscle.

More specifically, as FIG. 4 expands on FIG. 3, initially a scan of a target muscle 106 is received, block 302. An exemplary scan such as scan 500 is shown in FIG. 5. As previously shown and described with respect to FIG. 2, scan 500 includes skin and or other surface tissue 202, deep tissue 204 and target muscle tissue 206, with elements of non-muscle tissue 208. The muscle fuel 502 within scan 500 is conceptually shown to be high by the use of large dots 504 providing a substantially dark appearance to the scanned portion of the target muscle tissue 206.

As described above, and not being bound by any one theory, muscle fuel includes a number of water-bound constituents, like glycogen, building-block proteins, carnitine and creatine. In fact, each gram of glycogen is tightly bound to three grams of water, such that water content of a muscle can be correlated to a glycogen content of a muscle. Further, other muscle fuel constituents are also tightly-bound to water, some at a one gram to one gram ratio, allowing not just glycogen, but muscle fuel to be correlated with water content of a muscle. As further discussed herein, water allows sound waves to pass through without resistance and shows as hypoechoic (as compared to dense materials which are hyperechoic), which allows for the development of fuel concentration scales 506. Water, and therefore muscle fuel, is located in darker areas of an image, while lighter areas of an image are found to have less water and therefore less muscle fuel.

A pre-established fuel concentration scale 506 is also shown. The pre-establishment of the fuel concentration scale 506 aids in the effective identification of attributes that are correlated to the fuel, e.g., color, contrast, darkness, luminance and or combinations thereof.

In at least one embodiment, a precise reference of fuel values as a gradient scale is established by contemporaneously taking an ultrasound cross sectional image and a biopsy of the same target muscle at systematic stages of exercise to exhaust the fuel, and or fuel replenishment to re-establish the muscle fuel. The empirical data from a plurality of subject can establish an advantageous reference that is applicable to many different subjects.

It is also understood and appreciated that in at least one embodiment, an even more precise predetermined reference can be established for a specific subject by the contemporaneous imaging and biopsy process upon that subject. Alternatively, a general fuel concentration scale 506 as established from one or more other subjects may be refined for a specific subject based on repeated application of the methods 300/350/400 and or SNDGS 100.

As shown the fuel concentration scale 506 covers a range. For ease of illustration and discussion the exemplary range as shown is from 4 to 0. An actual range as applied in methods 300/350/400 and or in SNDGS 100 may be greater or smaller. For purposes of the exemplary embodiments and description thereof, the valuation of 4 is appreciated to be a fuel level of about 100% (e.g., the target muscle is at its maximum glycogen store) and a valuation of 0 is appreciated to be a fuel level of about 0% (e.g., the target muscle has depleted its glycogen store).

Moreover, as is further discussed below, the fuel scale—whether pre-established for a specific subject, or based more generally upon data from a plurality of test subjects permits a user of SNDGS 100 to advantageously and non-invasively determine the fuel within a target muscle 106. It should also be appreciated that this determination may be made upon a subject in nearly any setting or environment. In other words SNDGS 100 may be used and the fuel determined in a real time setting, for example, where the subject either is about to engage in an endurance activity or is engaged in training for endurance activity.

To evaluate the fuel 502 within the muscle tissue 206, method 400 proceeds by defining a plurality of regions within the scan 500. In at least one embodiment the plurality of regions or parts are a plurality of areas, block 402. These regions or areas can be defined in a variety of ways.

For at least one embodiment, pre-existing scan elements are accepted as the scan areas, as indicated by optional dotted block 404. In varying embodiments these pre-existing scan elements are one or more scan pixels. Where the scan is treated as an image, scan pixels may correlate directly with image pixels and image pixels may be used as the pre-existing elements.

Figure 6:
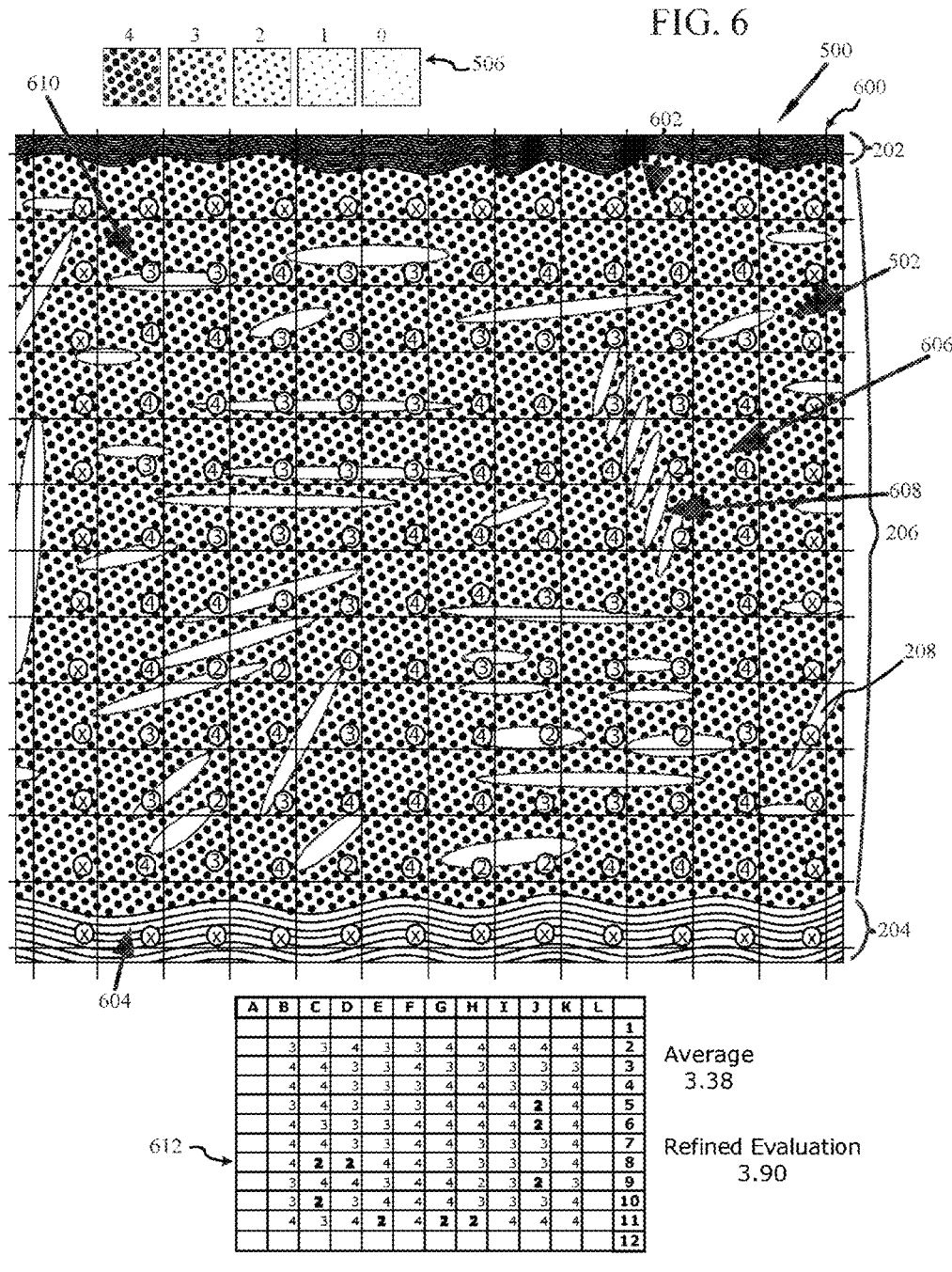
FIG. 6 is a conceptual illustration of the ultrasound scan of FIG. 5 with a grid and area attribute valuations in accordance with at least one embodiment.

In an alternative embodiment, as shown in FIG. 6 the plurality of areas are defined by applying a grid 600 to the scan 500. For ease of illustration and discussion the scan 500 is shown as an image, but it is understood and appreciated that the evaluating operation may be performed by working with the scan 500 as an image or as simply data, neither of which is actually displayed to an operator.

To summarize, for at least one embodiment the evaluating of at least a portion of the ultrasound scan 500 includes defining a plurality of areas within the ultrasound scan 500, each area having at least one attribute.

As shown in FIG. 6 the grid 600 is conceptually illustrated as a 12×12 grid for ease of illustration, thereby providing one hundred and forty four areas 602. In varying embodiments a larger or smaller grid may be applied. As is further shown in FIG. 6 a subset of the areas 602 is then selected, block 408.

Moreover, it is not unusual for the sides of the scan to be somewhat unclear, and as shown in FIGS. 5 and 6 there is both surface tissue 202 and deep tissue 204 partially captured in the scan 500 in addition to the desired muscle tissue 206. These undesired areas, of which area 604 is exemplary, are therefore removed from further consideration as indicated by the presence of a circled-X in each undesired area.

If not previously set, at least one attribute of the areas 602 is then selected, such as color, luminance, darkness, contrast or other identifiable attribute and/or combinations thereof, block 410. Moreover, the ultrasound scan as a data file may well contain information that although highly beneficial and adaptable for the determination of fuel is blurred or otherwise rendered less clear when the scan is rendered as an actual image to an operator. As such, it is understood and appreciated that non-visual attributes as well as visual attributes may also be utilized alone or in combination with one another in varying embodiments for the non-invasive determination of muscle fuel.

In at least one embodiment the attribute of comparison is hypoechoic appearance as opposed to hyperechoic (also known as echogenic) appearance. More simply stated the evaluation is a comparison of the attributes within an area 602 to a scale of black to white. Again for illustrative purposes the attribute selected in the present example is dot size.

With respect to FIGS. 5 and 6, it is clear that the presence of non-muscle tissues 208 affect the apparent concentrations of fuel, e.g., the dots, in some areas but not others. More specifically, exemplary area 606 is shown to have no non-muscle tissue 208 while exemplary area 608 has a substantial non-muscle tissue 208 component. In at least one embodiment, the identification and discounting of non-muscle tissue 208 is achieved. Moreover this advantageous identification and discounting can be achieved through the use of a threshold in area evaluation.

To simplify the initial walk through of method 400, initially the threshold will not be set, decision 412.

Method 400 therefore proceeds to select an area 610 that has not been removed from further consideration, block 414. The attribute of this area 610 is then quantified as a value, block 416. More specifically the attribute of the selected area 610 is compared to the fuel concentration scale 506 and an appropriate value assigned to the area 610, shown as the value within the circle—a 3 in the case of area 610. For example exemplary area 606 is quantified as a 4 whereas exemplary area 608 is quantified as a 2.

Method 400 proceeds with a query as to whether there are remaining areas to be quantified, decision 418. If additional areas remain, a new area is selected, block 420 and the attribute(s) are again quantified, block 416. In at least one embodiment, the selection of the next element is based on a sweep operation, e.g., starting at the far left and moving across an entire row before moving then to the next row and starting again at the far left. This sweep methodology can of course be adapted to move from right to left and from top to bottom or bottom to top of columns. The sweep method of selection is merely exemplary and is not a limitation precluding alternative selection schemes. Indeed, in at least one embodiment utilizing multiple processors and/or processes the selection and evaluation of all areas may be performed substantially simultaneously.

To summarize again, the evaluating of at least a portion of the ultrasound scan 500 includes, for at least a subset of defined areas 602, quantifying each attribute as a value from a predetermined range of values.

With the attributes of all areas now quantified as values, the values are processed to determine a fuel value for the target muscle 106 as scanned and represented by scan 500, block 422. Collectively, the values assigned to the attributes represent a data set. For at least one embodiment the processing of the values is an action to determine the central tendency of the data set.

Determining the central tendency of a set identifies the "center" of the distribution of values within the sets. There are three general types of estimates of central tendency and they are respectively, the mean, the median and the mode. To compute the mean, it is generally understood to take the sum of the values and divide by the count. This is commonly known as averaging. The median is the score found at the middle of the set of values, which is to say that there are as many cases with a larger value as there are cases with a smaller value. The mode is the most frequently occurring value in the set, e.g., the value occurring with the greatest frequency.

Other options for statistical measures of the values by processing them may also be performed such as standard deviation and range. Even for an average, there are three common choices—arithmetic mean (sum divided by count), the geometric mean (n member are multiplied together and then taking the nth root), and the harmonic mean (for a set s of numbers $a_1, a_2, \ldots a_a$ it is the reciprocal of the arithmetic mean of the reciprocals of a/s).

For various embodiments, processing of the values may also include the application of a constant value or other formula. In general and for the varying embodiments employing different forms of processing for the quantified values, the intent is to achieve a value that is representative of the amount of fuel within the target muscle as represented by the scan of the muscle tissue.

In at least one embodiment the processing of the values is averaging the values, e.g., an arithmetic mean. Moreover, in FIG. 6 a table 612 is shown with columns A to L and rows 1 to 12 correlating to the defined areas 602 of scan 500. The quantified values of the selected attribute for each area are shown and the overall average is shown to be 3.38. Based on the fuel concentration scale 506 the determined value of 3.38 at time $X_1$ is understood and appreciated to be a high fuel value.

The determined fuel value is then returned, block 424. In varying embodiments the determined value may be returned to the operator as the quantified value, or as a representation of the value—such as but not limited to color, sound, vibration, or combinations thereof as well as varying intensity thereof.

Use of SNDGS 100 and or method 300/350/400 has many practical applications, not the least of which is to assist in athletic and/or endurance training. Another application is for rehabilitation wherein it is highly desirable to quantify how the muscle tissues are repairing and/or rebuilding. Further still, another application would potentially benefit incapacitated subjects, such as hospital patients, the infirm, the elderly or other persons who may for one reason or another have difficulty communicating. As such, for at least one embodiment, the method and or use of SNDGS 100 may be repeated over time upon the same target muscle 106.

Figure 7:
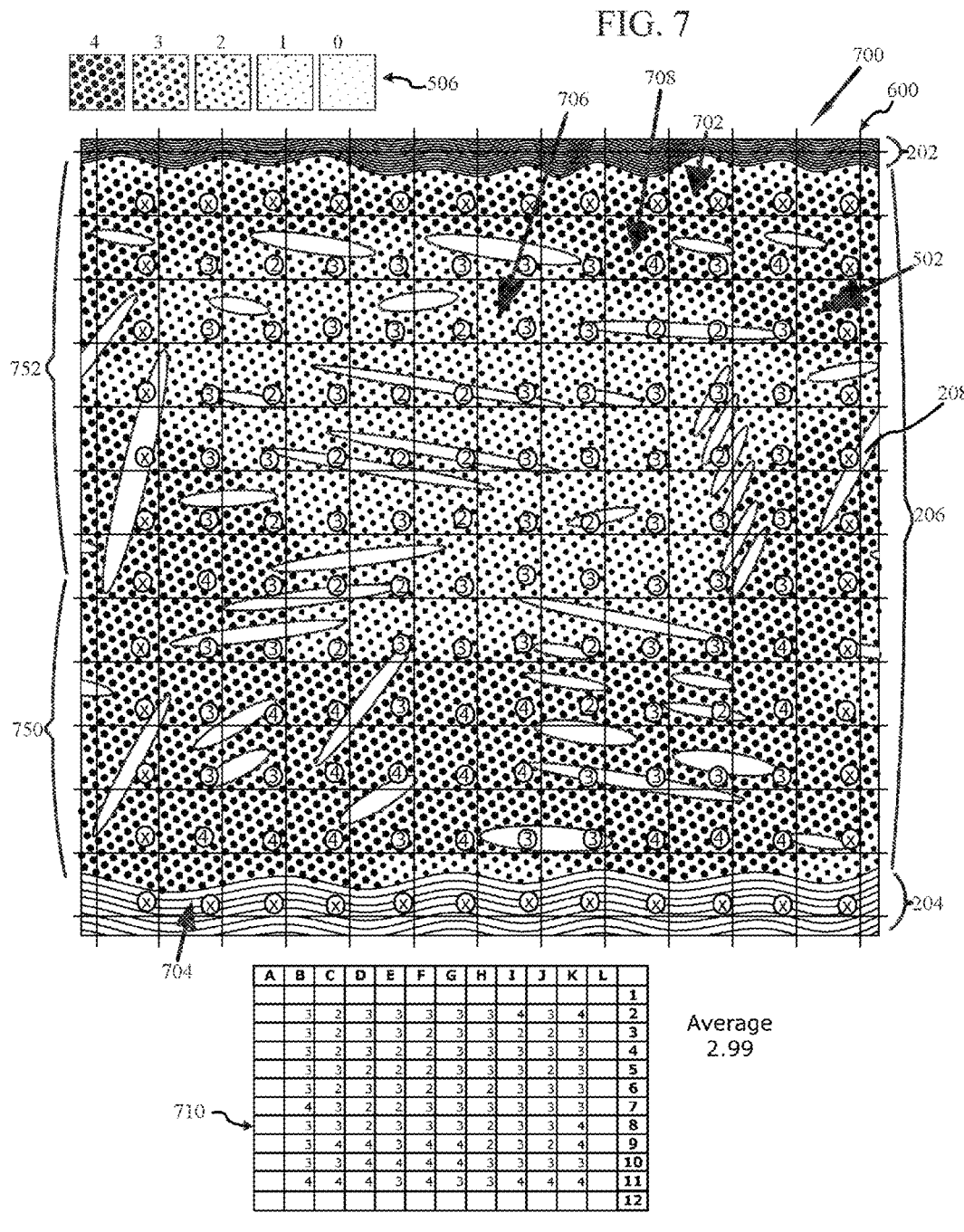
FIG. 7 is a conceptual illustration of an ultrasound scan of a target muscle at a second time interval with a grid and area attribute valuations in accordance with at least one embodiment.
Figure 8:
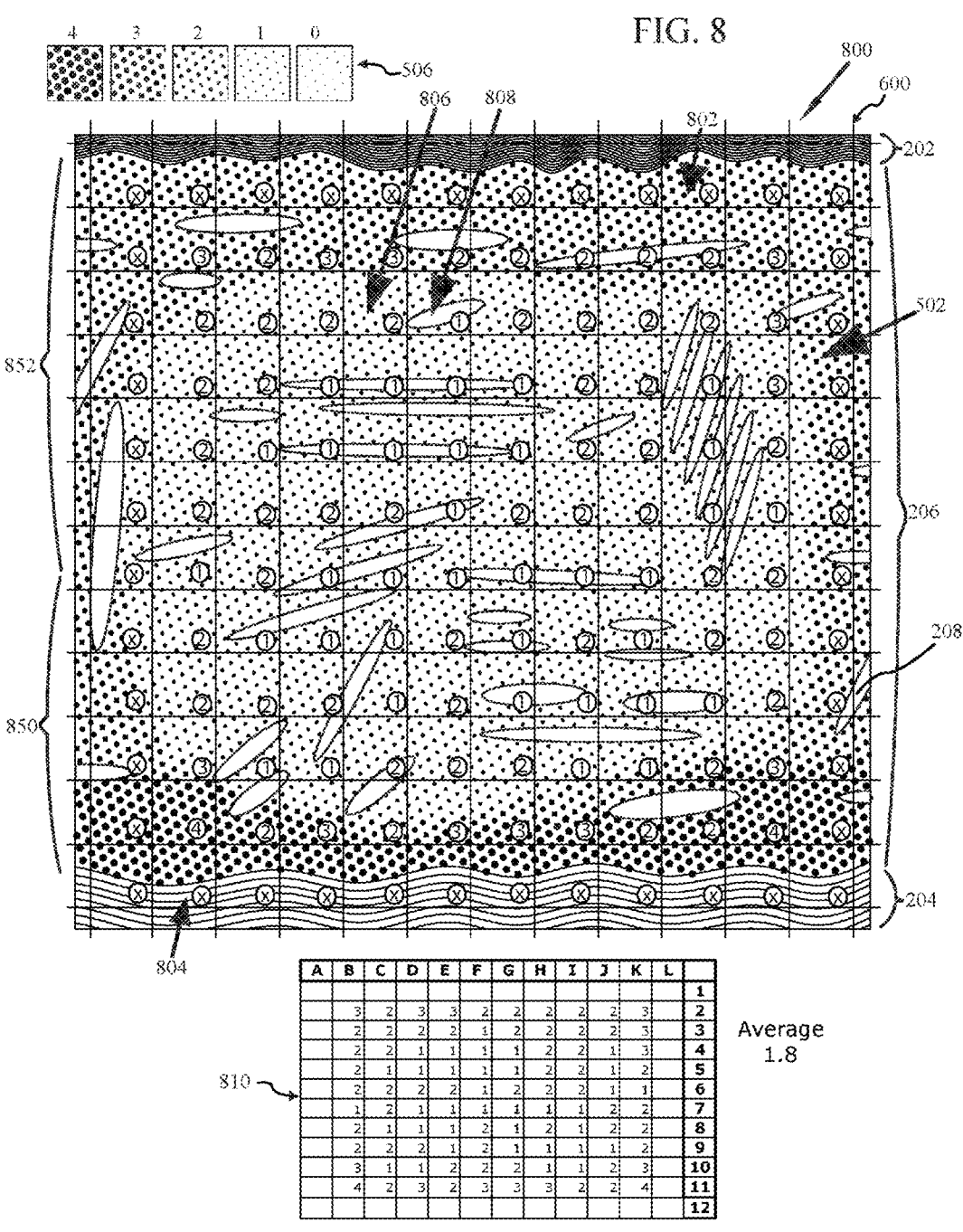
FIG. 8 is a conceptual illustration of an ultrasound scan of a target muscle at a third interval a grid and area attribute valuations in accordance with at least one embodiment.
Figure 9:
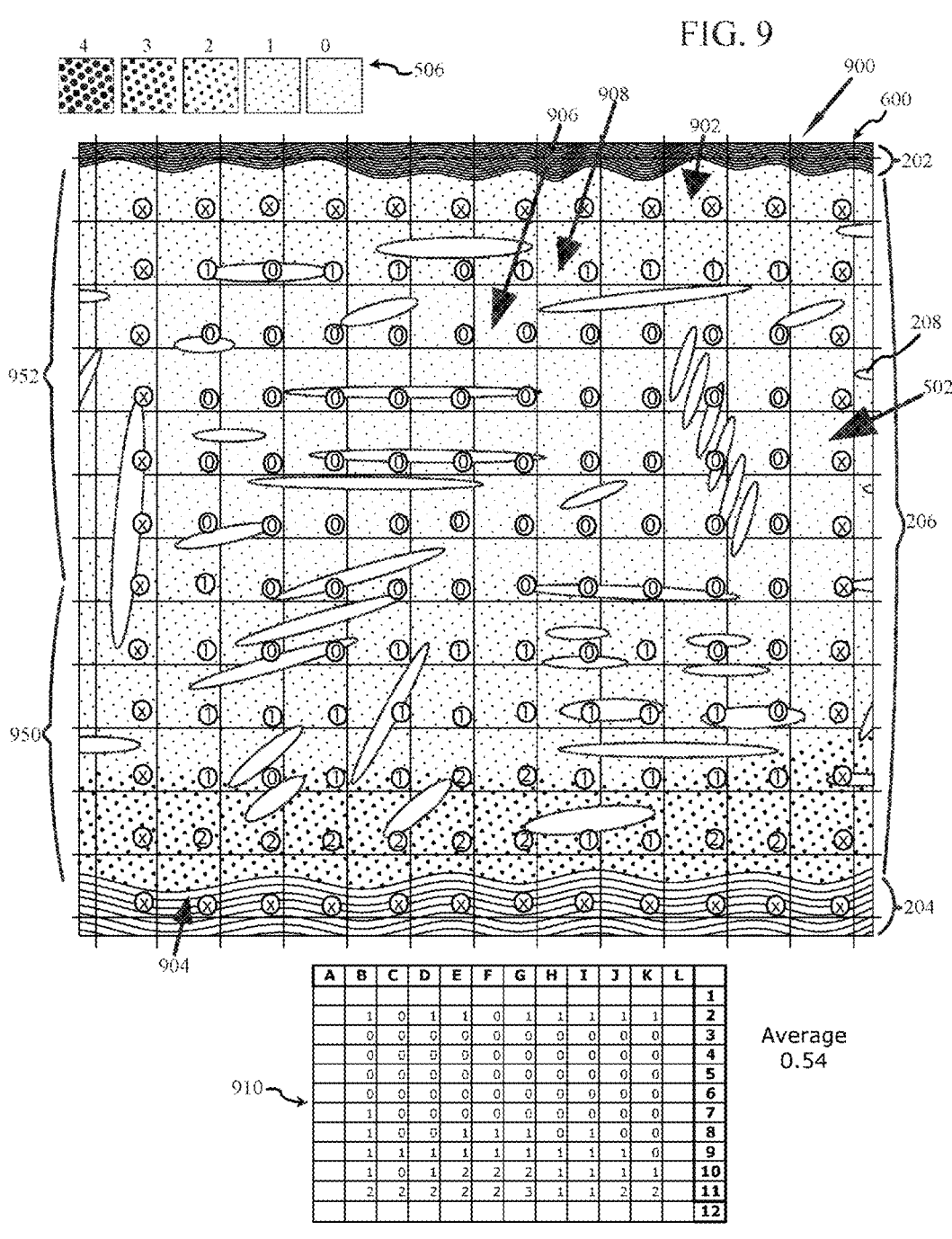
FIG. 9 is a conceptual illustration of an ultrasound scan of a target muscle at a fourth interval a grid and area attribute valuations in accordance with at least one embodiment.

FIGS. 7-9 conceptually illustrate repeated testing upon the same target muscle at time intervals of X during a subject's workout. As such, not only do FIGS. 6-9 cooperatively work to demonstrate how the method and or use of SNDGS 100 can advantageously assist in establishing an understanding of a subject's fuel values over time during exercise, each of FIGS. 6-9 when compared with the other FIGS. 6-9 also can help aid in understanding how the method and or use of SNDGS 100 can advantageously identify the fuel within a target muscle 106 as the fuel itself likely varies in concentration within the target muscle.

Further too, it will be observed that the non-muscle tissue 208 varies from location to location as between FIGS. 6-9. Moreover the methods and or use of SNDGS 100 can provide a non-invasive determination of fuel within a target muscle 106 even as the scan of the target muscle 106 may vary somewhat from one scan to the next.

Moreover, at the second time interval $X_2$, as shown in the scan 700 of FIG. 7, the fuel 502 in the deeper portion 750 of the target muscle 106 is still generally high. The fuel 502 in the outer portion 752 of the target muscle 106 tissue are beginning to diminish. Indeed prior to the onset of testing of the methods disclosed herein, it was unknown as to whether fuel depleted evenly throughout, from the outside in or the inside out.

Indeed, although a biopsy of the target muscle can be performed to detect glycogen (or other like energy constituents), based on the preliminary findings from test applications of this method it is clear that even a biopsy could be misleading—for if the biopsy is taken from too deep or too shallow a location within the target muscle, the sample may or may not accurately represent an overall evaluation of the target muscle as a whole. For at least one embodiment where a biopsy is performed contemporaneously with the scan of a target muscle such as to establish a baseline for a given subject, the location of the biopsy within the scan is noted so as to correlate the results of the biopsy to a specific area of the scan and thereby permit relative valuation to the other areas of the scan, e.g., areas 602, 702, 802, 902 based on the results of the biopsy.

Advantageously, and quite distinct from the biopsy, as the entire method is performed as a non-invasive process, there is no insult to the target muscle and therefore no real prospect of the test itself hampering performance. Further still, it is possible to quickly and easily compare in near real time the fuel values of different muscles, e.g. the subject's right rectus femoris muscle and the subjects left rectus femoris muscle. Such information may be highly advantageous during the rehabilitation of a muscle or group of muscles.

In other words, the method and or use of SNDGS 100 can enhance the evaluation of fuel within the target muscle that cannot easily be achieved, if at all matched strictly with muscle biopsy.

As with FIG. 6, a grid 600 has been applied to the scan 700 to define a plurality of areas 702 within the scan 700. Fuel 502 is again represented as dots of varying sizes. Undesirable areas, of which area 704 is exemplary, are again removed from consideration as indicated by the circle-X.

In accordance with the application of method 400, an area, such as exemplary area 706 is selected and the attributes of this area 706 are compared to the fuel concentration scale 506 and an appropriate value assigned to area 706, blocks 414 and 416. For example, exemplary area 706 is quantified as a 3 whereas exemplary area 708 is quantified as a 4.

Again, method 400 proceeds with a query as to whether there are remaining areas to be quantified, decision 418. If additional areas remain, a new area is selected, block 402 and the attribute(s) are again quantified, block 416.

As in FIG. 6, with the attributes of all areas now quantified as values, the values are processed to determine a fuel value for the target muscle 106 as indicated by scan 700. In at least one embodiment, the processing of the values is averaging the values. Moreover, in FIG. 7 a table 710 is shown with columns A to L and rows 1 to 12 correlating to the defined areas 702 of scan 700. The quantified values of the selected attribute for each area are shown and the overall average is shown to be 2.99, and indeed a reduction from the scan 500 at time X₁.

In FIG. 8 representing scan 800 at time interval X₃, brief observation indicates that both the deeper portion 850 and the outer portion 852 of the target muscle 106 are showing decreased fuel amounts 502.

As with FIGS. 6 and 7 a grid 600 has been applied to the scan 800 to define a plurality of areas 802 within the scan 800. Undesirable areas, of which area 804 is exemplary, are again removed from consideration as indicated by the circle-X.

Again in accordance with the application of method 400, an area, such as exemplary area 806 is selected and the attributes of this area 806 are compared to the fuel concentration scale 506 and an appropriate value assigned to area 806. For example, exemplary area 806 is quantified as a 2 whereas exemplary area 808 is quantified as a 1.

Again, method 400 proceeds with a query as to whether there are remaining areas to be quantified, decision 418. If additional areas remain, a new area is selected, block 402 and the attribute(s) are again quantified, block 416.

As in FIGS. 6 and 7, with the attributes of all areas now quantified as values, the values are processed to determine a fuel value for the target muscle 106 as indicated by scan 800. In at least one embodiment the processing of the values is averaging the values. Moreover, in FIG. 8 a table 810 is shown with columns A to L and rows 1 to 12 correlating to the defined areas 802 of scan 800. The quantified values of the selected attribute for each area are shown and the overall average is shown to be 1.8, and indeed a reduction from the scan 700 at time X₂.

In FIG. 9 representing scan 900 at time interval X₄, brief observation indicates once again that both the deeper portion 950 and the outer portion 952 of the target muscle 106 are showing decreased fuel 502.

Once again, as with FIGS. 6, 7 and 8 a grid 600 has been applied to the scan 900 to define a plurality of areas 902 within the scan 900. Undesirable areas, of which area 904 is exemplary, are again removed from consideration as indicated by the circle-X.

Again in accordance with the application of method 400, an area, such as exemplary area 906 is selected and the attributes of this area 906 are compared to the fuel concentration scale 506 and an appropriate value assigned to area 906. For example, exemplary area 906 is quantified as a 0 whereas exemplary area 908 is quantified as a 1.

Again, method 400 proceed with a query as to whether there are remaining areas to be quantified, decision 418. If additional areas remain, a new area is selected, block 402 and the attribute(s) are again quantified, block 416.

As in FIGS. 6, 7 and 8 with the attributes of all areas now quantified as values, the values are processed to determine a fuel value for the target muscle 106 as indicated by scan 900. In at least one embodiment, the processing of the values is averaging the values. Moreover, in FIG. 9 a table 910 is shown with columns A to L and rows 1 to 12 correlating to the defined areas 902 of scan 900. The quantified values of the selected attribute for each area are shown and the overall average is shown to be 0.54, and indeed an even further reduction from the scan 800 at time X₃.

With respect to FIGS. 6-9, it is understood and appreciated that as substantially the same grid 600 is applied to each scan, e.g., scans 500, 700, 800 and 900, the same number of areas are defined within each scan, and the size of the defined areas is generally constant from one scan to the next. This consistency remains and is not affected by different locations of the scan. Certainly for consistency it is desirable for the operator to attempt to be close and perform each scan in approximately the same location—but slight variation of location is not detrimental.

Figure 10:
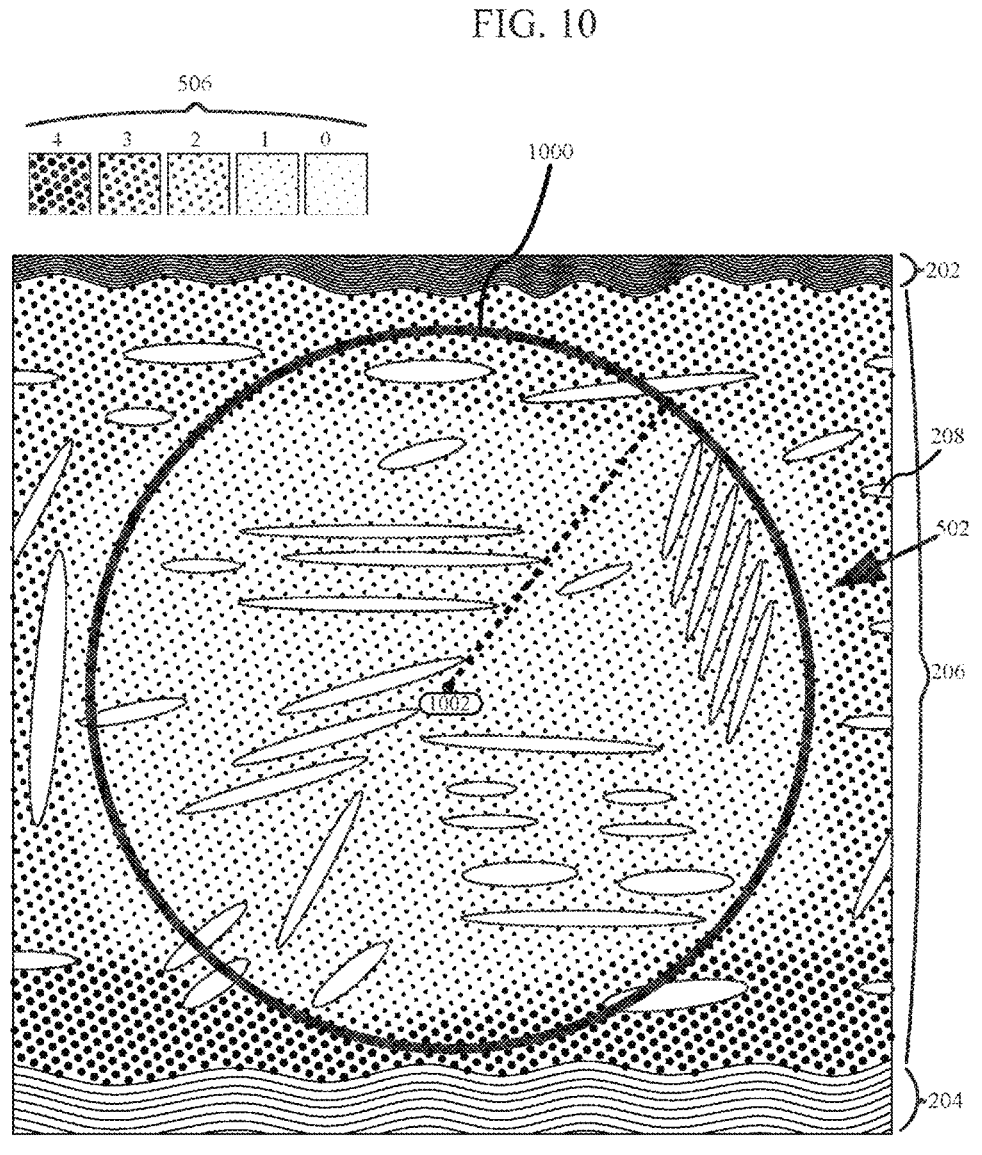
FIG. 10 is a conceptual illustration of an ultrasound scan of a target muscle further showing an automated selection of an area for evaluation in accordance with at least one embodiment.

In addition, in FIGS. 6-9 and with respect to the evaluating operation of method 400, it has been noted above that undesirable areas are removed from consideration. In at least one embodiment, the selection of the subset of areas for quantified valuation is an automated process. More specifically, as shown in FIG. 10, in at least one embodiment the selection of the portion 1000 for evaluation is determined based upon the center 1002 of the scanned image of the target muscle 106. In alternative embodiments, the portion 1000 could also be offset from the determination of the skin and outer tissue layers or by other generally established reference point.

Figure 11:
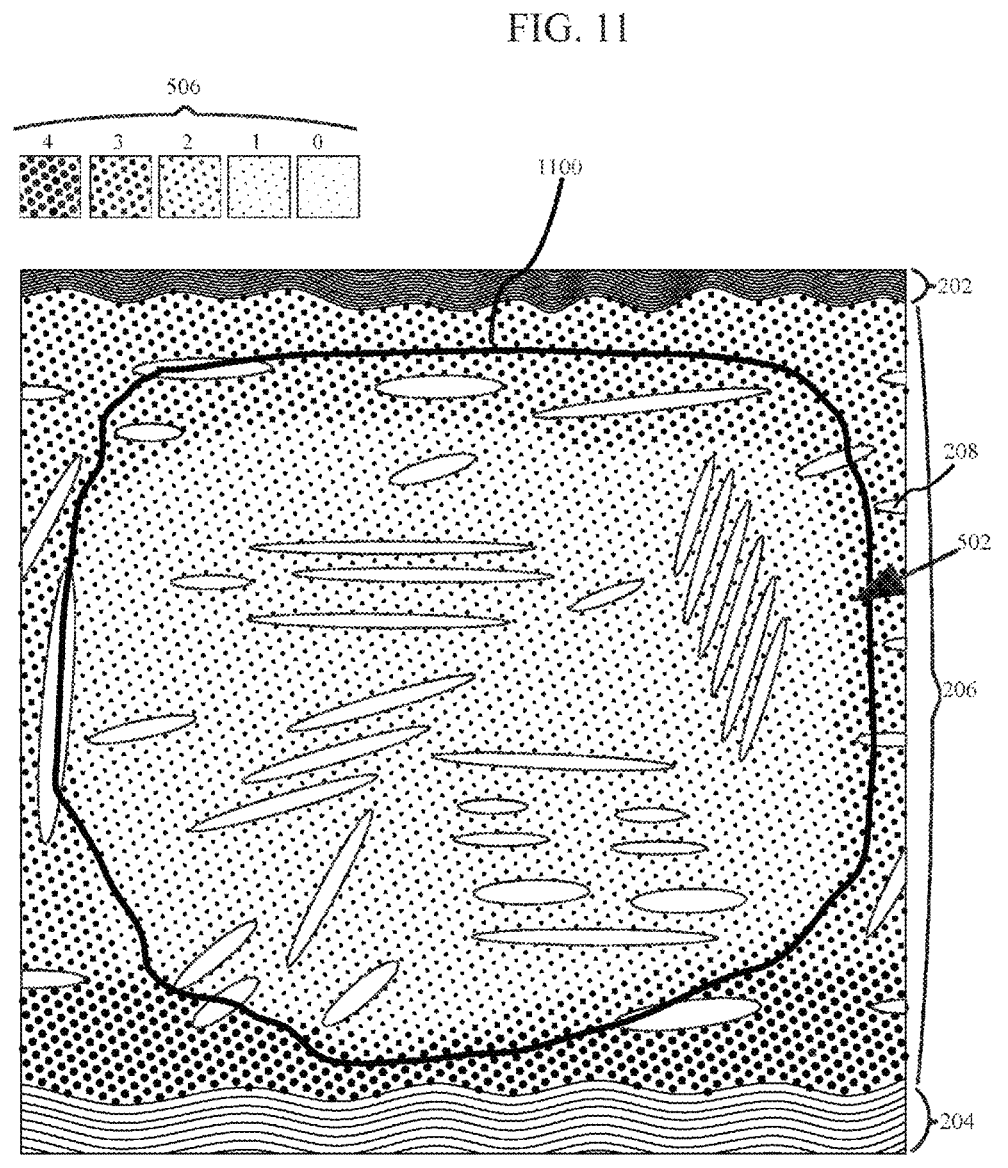

In at least one alternative embodiment, the selection of the portion for evaluation is user adjustable and or definable. More specifically, for at least one embodiment as shown in FIG. 11, the operator can indicate by a drawn line 1100 the boundary for the selected portion for evaluation. In yet other alternative embodiments, line 1100 may be achieved by stretching and otherwise altering the initial automated selection, such as portion 1000 in FIG. 10.

Figure 12:
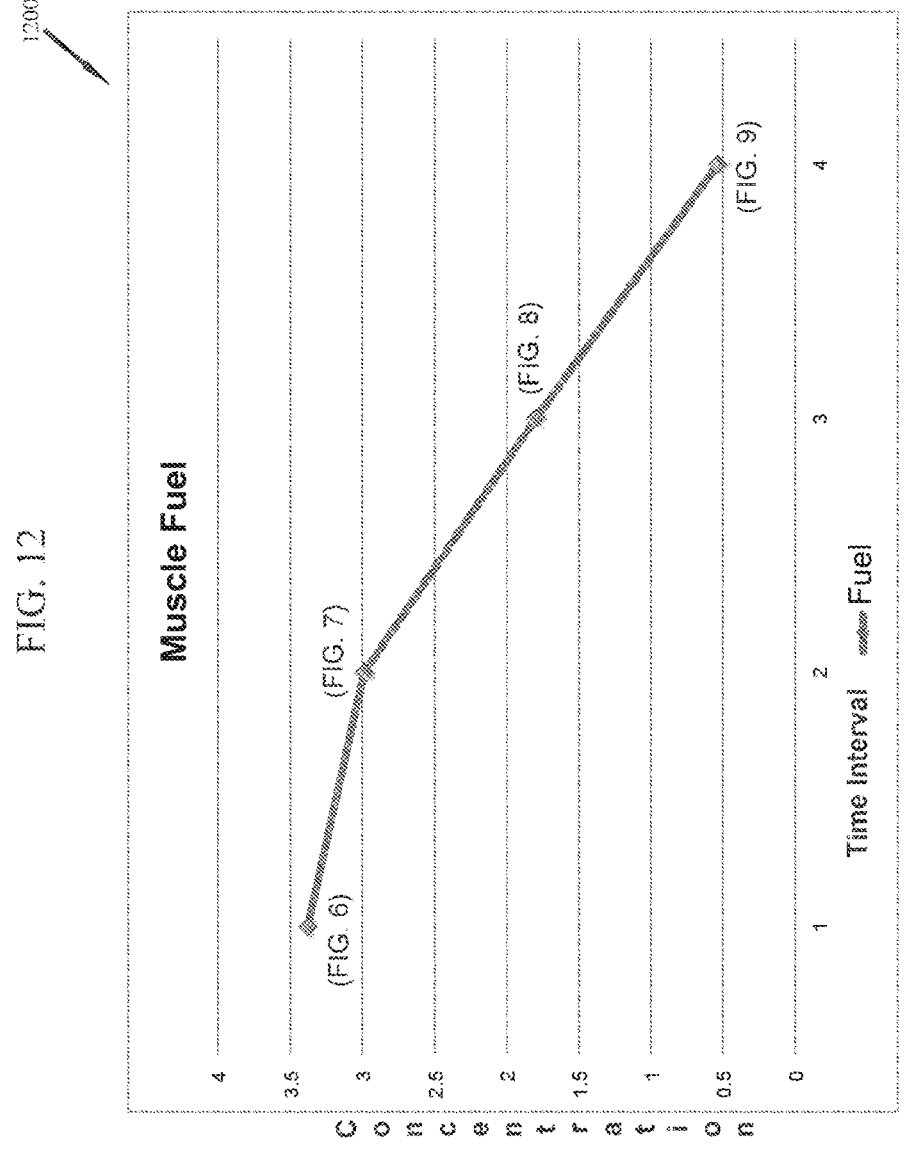
FIG. 12 is a chart of the determined fuel values as determined in FIGS. 6, 7, 8 and 9 in accordance with at least one embodiment.

FIG. 12 presents a chart 1200 of the determined fuel for times X₁ to X₄ as shown in FIGS. 6 to 9. Such testing and the resulting chart 1200 can be an advantageous tool in athlete conditioning. For example, use of the method and or SNDGS 100 prior to the onset of training and during training can assist the athlete subject in maximizing his or her training efforts, for attempting to exercise or compete with diminished fuel can accelerate muscle breakdown, increase the possibility of injury, and potentially subject the subject to other undesirable conditions.

Moreover, application of the methods and or SNDGS 100 can help determine whether the subject should eat more carbohydrates, drink more water, take energy supplements before exercising or competing, whether his or her fuel amounts are good and further eating would only divert blood from the muscles to the stomach for digestion, and or whether despite eating the subject's muscles are not in an optimal condition for exercise or competition and rest should be enjoyed.

Further, as SNDGS 100 permits substantially real time analysis of muscle fuel, a base line for a subject's metabolism and conversion of foods to fuel stores can be established. More specifically, by having a subject eat food, such as but not limited to bread, fruit, energy supplements such as gels, formulated bars, etc., and scanning one or more target muscles during and after the consumption, SNDGS 100 permits the subject to advantageously know his or her precise conversion scale for "X" grams of carbohydrates (for example) to a "Y" valuation of fuel in a given amount of time.

Such knowledge of how many grams of carbohydrates equate to a maximum fuel storage value, and/or the replenishment of that value is highly advantageous in many settings. A coach can monitor and adjust the food intake of his or her individual or team athlete(s), but so too can military personnel better prepare for mission critical situations. More specifically, by forecasting the duration of a mission and the level of exertion during that mission, a commander can accurately predict how much food each member of the team should have, for too little and the mission may suffer due to fatigue or lack of optimum performance and too much may adversely add unnecessary bulk and weight to a team that is striving to move with speed and stealth. The same can be said for the amount of water that should be ingested to maximize fuel intake values to the muscle. Users of the embodiments herein can monitor any number of parameters to optimize performance and maximize fuel amounts in target muscles.

As SNDGS 100 and/or methods 300/350/400 permit the determination of fuel values within one or multiple muscles, it will be appreciated that SNDGS 100 and methods 300/350/400 may be adapted so as to identify for a target muscle a target fuel score. In addition, different muscles within a subject's body may be better indicators of muscle fuel values then others and this too may be determined. For example in subject A, the muscle of interest may be his left bicep, but his left vastus lateralis is a better indicator muscle. For subject B, the muscles of interest may be both the left and right vastus lateralis, but the right rectus femoris is a better indicator muscle. This may be due to differences in the size of the muscles and or differences in person to person physiology.

Although it is certainly possible to exercise one muscle and not another and thereby reduce the fuel within one muscle but perhaps not as significantly in other muscles, the re-development of fuel within the muscles, especially when at rest—is a process based on the circulatory systems delivery of nutrients and is therefore generally balanced throughout the body. Indeed, although all muscles fuel values are independent of one another, all of the muscle fuel do relate to the total fuel in the body.

As such, identifying different ranges for fuel in different muscles can assist in better evaluating the fuel values in one or more desired muscles. More simply stated, one or more indicator muscles may be identified within a subject's body and may then be used to better evaluate the subjects muscle fuel values both individually and with respect to the total body muscle fuel.

Figure 19:
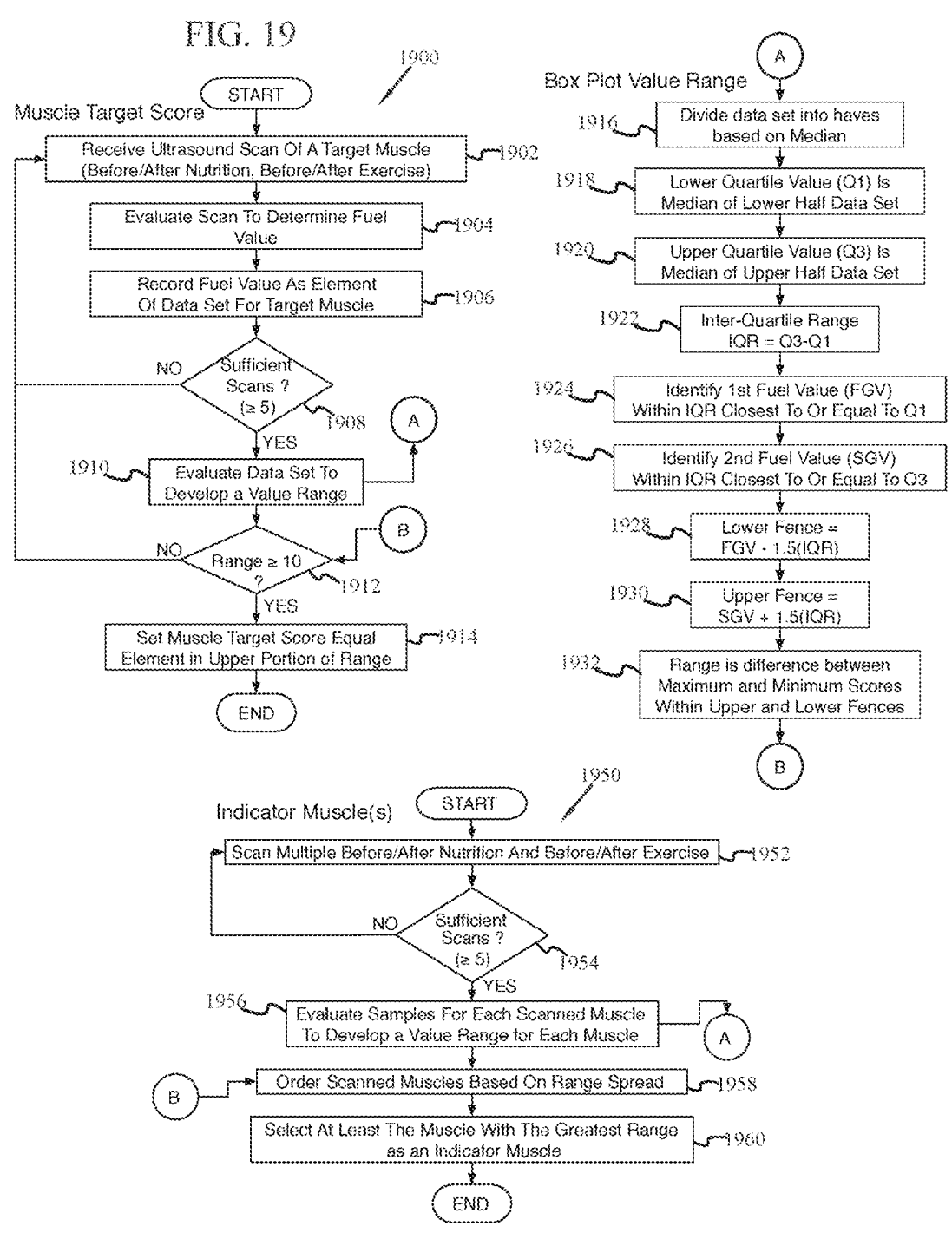
FIG. 19 illustrates flow charts for determining both muscle target scores and indicator muscles in accordance with at least one embodiment.

FIG. 19 presents a flow diagram for a method 1900 in accordance with at least one embodiment for determining a target fuel score. As indicated it is most ideal to scan the target muscle before and after nutrition as well as before and after exercise so as to develop a more complete fuel profile for the target muscle. Method 1900 commences by scanning a target muscle as described above to receive an ultrasound scan, block 1902. The scan is then evaluated as described above so as to determine a fuel value, block 1904. The fuel value is then recorded as an element of a data set for the target muscle, block 1906. Whereas the above description utilized a range of 4 to 0 for ease of discussion and illustration, for at least one embodiment the range is 10 to 0, 50 to 0, and can also be 100 to 0.

Determination of a target score is facilitated by multiple scans so as to provide a greater identified range of potential muscle fuel values for the target muscle. As such for at least one embodiment, method 1900 queries the number of scans that have been performed, decision 1908. For at least one embodiment, if the number of scans is less than 5, method 1900 repeats for additional scans before continuing. Moreover, a single data point representing a fuel value is not generally sufficient by itself to define a range. Two different data points can define a range, but as the number of data points increases so too does the precise nature of the range.

If a sufficient number of scans have been performed, method 1900 continues by evaluating the data set to develop a range of fuel values, block 1910. Determination of a target score is facilitated by having a viable range, such as values spanning a pre-determined range. For at least one embodiment, the pre-determined range is equal to or greater than 10. If the determined range of actual values in the data set is less than the pre-determined range, method 1900 returns to collect more scans, decision 1912. In other words, for at least one embodiment method 1900 requires at least 5 scans as well as a range of at least 10 as defined by the at least five scans. If either condition is not true, method 1900 continues to collect additional scans until the conditions are satisfied. Of course it is understood and appreciated that in varying embodiments, a greater or lesser number of scans and a greater or lesser range may be adopted.

In the event that the ranges of values in the data set is equal to or greater than the pre-determined range, decision 1912, method 1900 advances to determining a target score based on an upper portion of the determined range, block 1914.

For at least one embodiment, evaluating the data set may be described as providing a statistical summary for the fuel value data set. Moreover, for at least one embodiment, the evaluation of the data set, block 1910, is more fully appreciated by the determination of quartile values and the use thereof.

Figure 20:
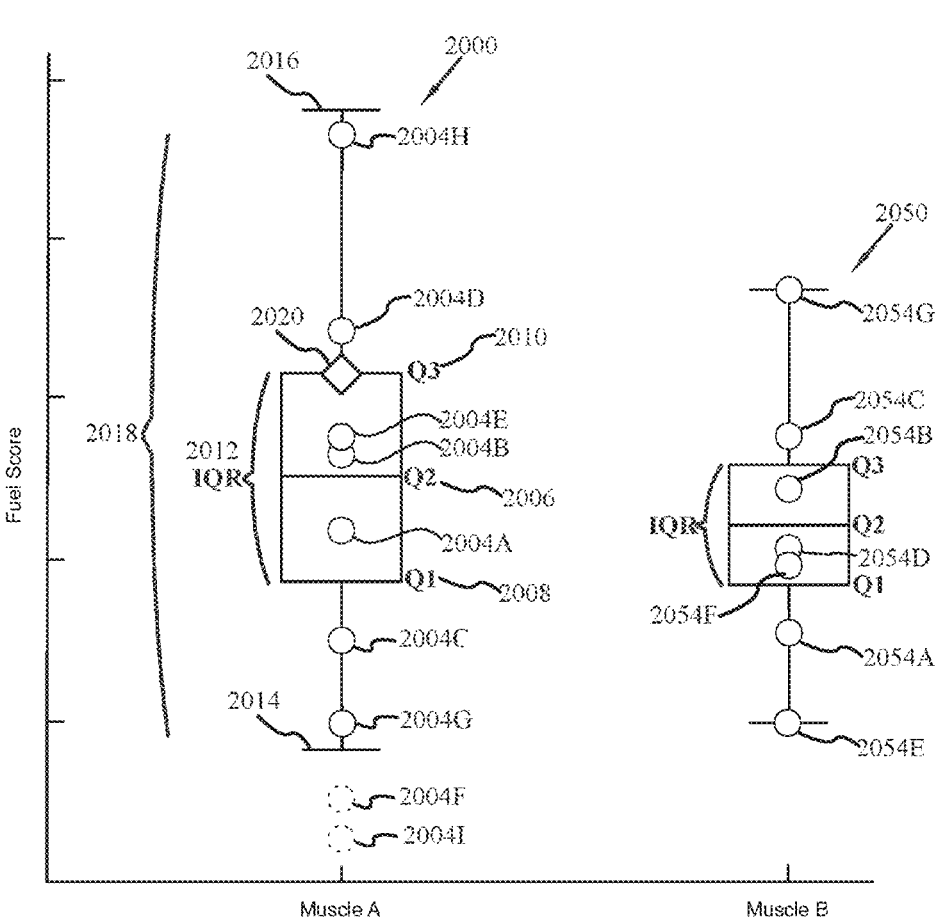
FIG. 20 conceptually illustrates box plots for two muscles so as to further illustrate the determination of target muscle scores as discussed with respect to FIG. 19 in accordance with at least one embodiment.

FIG. 20 illustrates a plot 2000 of an exemplary data set 2002 of data points 2004 for an exemplary muscle, Muscle A, and a plot 2050 of an exemplary data set 2052 of data points 2054 for an exemplary muscle, Muscle B. As shown for Muscle A, there are nine data points 2004A-2004I representing muscle fuel scores as determined from ten different scanning sessions. Muscle B has seven data points 2054A-2054G, defining a smaller plot 2050.

As illustrated, in at least one embodiment, the data set is divided into halves based on the median value (Q2 2006) of the data set, block 1916. A lower quartile value (Q1 2008) is determined as the median of the lower half of the data set, block 1918. An upper quartile value (Q3 2010) is determined as the median of the upper half of the data set, block 1920. An inter-quartile range (IQR 2012) is then established as the difference between Q3 2010 and Q1 2008, block 1922.

Depending on the actual elements of the data set 2002, Q3 2010 and Q1 2008 may or may not match to one or more actual elements of the data set 2002. Accordingly within the IQR 2012, the fuel value (FGV) equal to or above Q1 2008 is identified, block 1924. In FIG. 20, this is data point 2004A. Similarly, the fuel value (SGV) equal to or just below Q3 is identified, block 1926.

In FIG. 20, this is data point 2004E. A lower fence value 2014 is established as, Lower Fence=FGV−1.5 (IQR), block 1928, and an upper fence value 2014 is established as, Upper Fence=SGV+1.5 (IQR), block 1930. Data points correlating to muscle fuel values that are above the upper fence 2016 or below the lower fence 2014, such as data points 2004F and 2004I, are considered outliers and therefore discounted.

The range 2018 of fuel values for the target muscle is then established as the maximum and minimum actual fuel values within the upper and lower fences (e.g. fuel value data point 2004H and fuel value data point 2004G, block 1932). Of course it is understood and appreciated that in varying instances, actual data points may indeed correspond with the upper fence, the lower fence or both, such as is shown in the plot 2050 for Muscle B. For at least one embodiment, the target score, represented as a diamond 2020, for the target muscle is established as Q3 2010. Of course as additional scans are performed over time and as additional data points for determined fuel scores are added as elements to the data set, the precision of the defined range 2012 will be improved, as will the true value of Q3 2010.

The statistical summary of the data set for the target muscle may be displayed to a user as a box plot 2000 as shown in FIG. 20. As shown by FIG. 20, very quickly the use can appreciate the range 2018 of likely fuel values as well as the target score 2014. The data points that comprise the IQR are important because they not only determine the IQR values, but also the upper and lower fences.

To summarize, for at least one embodiment, determining a target fuel score 2020 for a target muscle includes receiving an ultrasound scan of a target muscle; evaluating at least a portion of the ultrasound scan to determine fuel value within the target muscle; recording the determined fuel value for the muscle as an element of a data set 2002 for the muscle; evaluating the fuel data set 2002 to determine a value range 2018; and in response to the range 2018 being at least above a pre-determined threshold, establishing a target score 2020 for the muscle as based on an upper portion of the value range. This value will be referred to as the fuel value for the muscle.

It should also be understood and appreciated that method 1900 may be performed in a somewhat historical fashion, wherein a plurality of existing scans for a target muscle over a plurality of ultrasounds scanning sessions are received and evaluated collectively. Moreover for at least one alternative embodiment determining a target fuel value 2020 for a target muscle includes receiving from a subject a plurality of ultrasound scans of a target muscle over a plurality of ultrasound scanning sessions; for each received ultrasound scan, evaluating at least a portion of the ultrasound scan to determine fuel value within the muscle, the collective fuel values being a fuel value data set 2002 for the muscle; evaluating the fuel value data set 2002 to determine a value range 2018; and in response to the range 2018 being at least above a pre-determined threshold, establishing a target score 2020 for the muscle as based on an upper portion of the value range.

As noted above, for a given subject different muscles may be better indicators of fuel levels then other muscles. For at least one embodiment, a similar scanning and evaluation process as described above with respect to method 1900 and FIG. 20 is performed upon the subject with respect to a plurality of difference muscles. This plurality of muscles may be based upon the nature of the subjects sport or conditioning, or may be based more generally on a collection of different major muscle groups. Moreover, for each muscle scanned, each scanned muscle is a target muscle for that scan.

Determining an indicator muscle may be an operation that is performed independently from the determination of a target score. As such for at least one embodiment, optional method 1950 commences with the scanning of multiple muscles as described above to determine a plurality of fuel values, each associated with a specific muscle, block 1952. The determined fuel value of each muscle is recorded to a database as an element of a data set associated with each muscle. Whereas the above description utilized a range of 4 to 0 for ease of discussion and illustration, for at least one embodiment the range is 100 to 0. Once again, it is most ideal to scan the muscles to occur before and after nutrition as well as before and after exercise so as to develop a more complete fuel profile for each of the scanned muscles.

Determination of an indicator muscle is facilitated by multiple scans so as to provide a greater identified range of potential muscle fuel values for each of the scanned muscles. As such for at least one embodiment, method 1950 queries the number of scans that have been performed for each muscle, decision 1954. For at least one embodiment, if the number of scans is less than 5, method 1950 repeats for additional scans of each muscle before continuing.

If a sufficient number of scans have been performed, method 1950 continues by evaluating the data set for each muscle to develop a range of fuel values for each muscle, block 1956. As the different muscles are being compared to one another so as to identify an indicator muscle, in at least one embodiment it is not necessary that each scanned muscle have a viable range of values spanning a pre-determined range as in the above case of determining a target score value.

The evaluated ranges are then ordered, or otherwise ranked to one another based on range spread, block 1956. And at least the muscle with the greatest range is selected as an indicator muscle, block 1960. It is understood and appreciated that if the specific muscle of interest is different from the indicator muscle, the desired muscle is not necessarily ignored. While scanning of the determined indicator muscle(s) may be sufficient in some situations to assess general muscle fuel, and may be sufficient in some situations, in others the use of the of at least one indicator muscle is combined with the evaluation of the desired muscle so as to enhance the evaluation of the fuel within the desired muscle. In other words, the indicator muscle may be used as a baseline for evaluating a muscle fuel value in a different muscle.

For at least one embodiment, evaluating the data sets may be described as providing a statistical summary for the fuel value data sets. Moreover, for at least one embodiment, the evaluation of the data sets, block 1956, is more fully appreciated by the determination of quartile values and the use thereof. Moreover, in at least one embodiment, the evaluation of the data sets includes for each data set the steps described above as blocks 1916-1932 for the determination of Q2, Q3, IQR, a lower fence and an upper fence. In addition, for each muscle a target score may also be identified as Q3.

Figure 21:
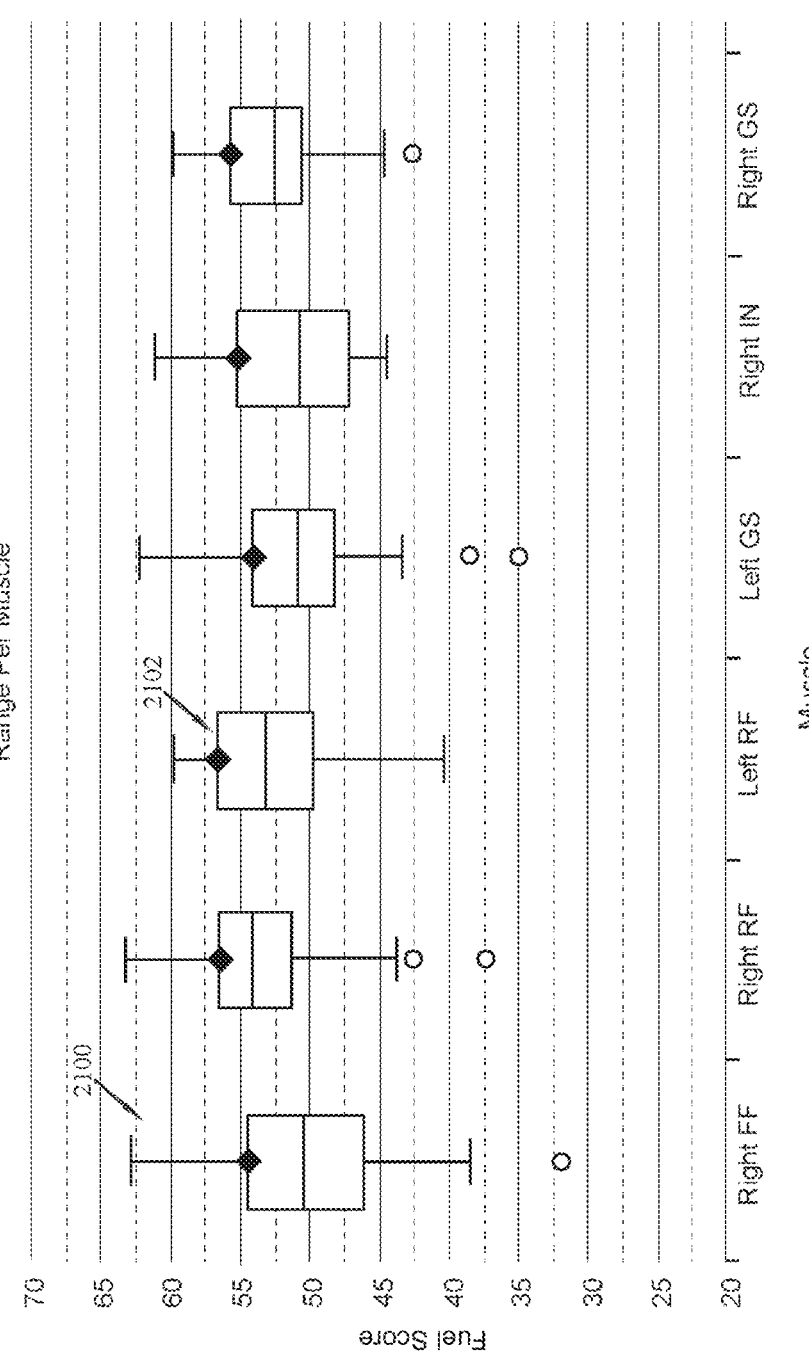
FIG. 21 conceptually illustrates box plots for a plurality of muscles so as to further illustrate the determination of indicator muscles as discussed with respect to FIG. 19 in accordance with at least one embodiment.

FIG. 21 presents an exemplary set of box plots established for a plurality of muscles so as to identify at least one indicator muscle to assist with the evaluation of a target muscle. These box plots represent scans for the Right FF (Right Forearm Flexors), Right RF (Right Rectus Femoris), Left RF (Left Rectus Femoris), Left GS (Left Gastrocnemius/Soleus), Right IN (Right Infraspinatus), and Right GS (Right Gastrocnemius/Soleus). As shown, the box plot 2100 for the Right FF muscle has the greatest range and is selected as an indicator muscle.

For the exemplary subject who's muscles are reflected in FIG. 21, general muscle fuel in his or her body may be quickly gauged by a scan of the Right FF as the indicator muscle. For evaluation of a specific desired muscle, such as the Left RF, shown to be box plot 2101, the scan of the desired muscle and the associated box plot may be compared with the scan and box plot of the indicator muscle. Moreover, for each muscle scanned the present value of the determined fuel value can be displayed upon the associated box plot for advantageous visual comparison and evaluation.

To summarize, for at least one embodiment, determining at least one indicator muscle for determination of muscle fuel, comprising: selecting from a subject a plurality of different muscles to establish a plurality of fuel value data sets, each data set established by; receiving an ultrasound scan of each muscle; evaluating at least a portion of the ultrasound scan to determine fuel value within the muscle; recording the determined fuel value for the muscle as an element of a fuel value data set for the muscle; evaluating each fuel value data set to determine a range for each muscle; ranking the scanned muscles by determined range; and selecting at least the highest ranked muscle as at least one indicator muscle.

It should also be understood and appreciated that method 1900 may be performed in a somewhat historical fashion, wherein a plurality of existing scans for a plurality of different muscles over a plurality of ultrasounds scanning sessions are received and evaluated collectively. Moreover for at least one alternative embodiment determining at least one indicator muscle for determination of muscle fuel value, comprising: receiving from a subject a plurality of ultrasound scans from a plurality of different muscles over a plurality of ultrasound scanning sessions; for each received ultrasound scan of each muscle, evaluating at least a portion of the ultrasound scan to determine fuel value within the muscle, the collective fuel values being a fuel value data set for the muscle; evaluating each fuel value data set to determine a range for each muscle; ranking the scanned muscles by determined range; and selecting at least the highest ranked muscle as at least one indicator muscle.

Moreover, it is understood and appreciated that methods 1900 and 1950 are for at least one embodiment, integrated as components of SNDGS 100 and/or methods 300/350/400. For at least one alternative embodiment, methods 1900 and 1950 are additional capabilities that may be separately engaged by SNDGS 100 and/or methods 300/350/400. For yet at least another embodiment, methods 1900 and 1950 are incorporated as specific capabilities for specific embodiments of SNDGS 100 and augmentations of methods 300/350/400. In other words, the identification of a target score for a target muscle and/or the identification of indicator muscles may be additional features provided for some enhanced embodiments.

Moreover, SNDGS 100 and/or methods 300/350/400/1900/1950 are for at least one embodiment adapted as a method of endurance conditioning for a subject. Specifically, during periods of endurance activity a coach, therapist, trainer, or other person—including the subject, can scan one or more target muscles at a plurality of intervals. Typically the first interval would be just before starting or at about the onset of the activity. By tensing the target muscle as noted above, a great consistency for the scan and evaluation is easily achieved. Based on the scan and its evaluation the endurance activity may be adjusted—such as to increase the level of activity, decrease the level of activity or perhaps even halt the endurance activity all together.

As the ultrasound scanning process is quick, and can be performed with hand held devices, discussed further below, SNDGS 100 and/or methods 300/350/400/1900/1950 can be performed in the field of the endurance activity. In other words the subject does not have to travel to a specific facility or location for the scanning and evaluation to be performed. For example a cyclist can pause on a trainer or even hold onto a moving car to permit the scan of a target leg muscle. A swimmer may rest at the edge of the pool or hop out briefly to permit the scan of a target muscle. A runner may pause on a treadmill or stop on the side of the road. A football, soccer, or other field athlete may permit a scan while he or she is out of rotation. A patient undergoing rehab may be scanned during the rehab. Moreover, the fuel levels of a subject may be non-invasively determined in a setting where such determination is highly advantageous and contemporaneously applicable to the performance of the endurance activity.

Returning to the FIGS. 5-9 and the evaluating operation as shown in FIG. 4, it is once again noted that throughout the muscle tissue 206 are elements of non-muscle tissue 208, such as but not limited to connective tissue, vascular tissue, scar tissue, foreign objects, etc. . . . In the initial review of method 400 it was noted that identifying and discounting of non-muscle tissue could be achieved and would likely enhance the precision for the determination of the fuel within the target muscle 106.

Returning to FIG. 4, and FIG. 6, in at least one embodiment this elimination of non-muscle tissue 208 is achieved through the application of a threshold in the area evaluation. For the initial pass, a threshold should to be set, decision 412. For at least one embodiment, the threshold may be a user provided value.

Establishing a threshold from the scan itself may be advantageous as the threshold is then individually determined from the scan and can vary from scan to scan, muscle to muscle, subject to subject etc. . . . while still maintaining high precision for evaluation.

In at least one embodiment where the threshold is individually determined from the scan, the method 430 of initializing the threshold substantially parallels the above description for the general determination of the fuel value with respect to block 410-block 418.

Moreover, the method 430 proceeds to select an area 602 that has not been removed from further consideration, block 432. The attribute of this area 602 is then quantified as a value, block 434. More specifically the attribute of the selected area 602 is compared to the fuel concentration scale 506 and an appropriate value assigned to the area 602. For example exemplary area 606 is quantified as a 4 whereas exemplary area 608 is quantified as a 2.

The method 430 of initializing the threshold proceeds with a query as to whether there are remaining areas to be quantified, decision 436. If additional areas remain, a new area is selected, block 438 and the attribute(s) are again quantified, block 416.

With the attributes of all areas now quantified as values, the values are processed to determine a fuel for the target muscle 106 as scanned and represented by scan 500, block 422. In at least one embodiment the processing of the values is averaging the values. Moreover, in FIG. 6 a table 612 is shown with columns A to L and rows 1 to 12 correlating to the defined areas 602 of scan 500. The quantified values of the selected attribute for each area are shown and the overall average is shown to be 3.38.

Although the threshold can be set to be the overall average, as different areas have different concentrations of fuel due to the presence or absence of non-muscle tissue 208 as well as state of the muscle tissue itself, in general for at least one embodiment the threshold is established as a percentage of the initial average value, block 440, such as for example 80%. Moreover, for at least one embodiment, evaluated areas having an attribute value of at least 3.07 (80% of 3.38) are considered muscle tissue while areas having an attribute value of less than 3.07 (80% of 3.38) are considered non-muscle tissue 208 and therefore eliminated from further consideration.

With a threshold so established, as each area is quantified under block 416, the quantified value is now compared to the threshold, in accordance with method refinement 450. For an embodiment where the same threshold is to be applied for the entire scan, the previously determined threshold is used, decision 452 and block 454. As will be further explained momentarily, in at least one alternative embodiment the threshold is adaptively varied, and more specifically is based the values of proximate areas, decision 452 and block 456.

Where the value of the attribute is above the threshold, e.g., greater than 3.07 (80% of 3.38), decision 458, the area and its associated value is maintained, block 460. Where the value of the attribute is below the threshold, e.g. smaller than 3.07 (80% of 3.38), decision 458, the area and its associate value are discarded, block 462. Moreover it is understood and appreciated that the value of the attribute is compared to the threshold. Incidental variations of the method to keep the value if equal to or above in one embodiment or to discard if equal to or below in an alternative embodiment are within the scope of this methodology.

For the example of FIG. 6 there are nine (9) areas with evaluated attributes rated as 2. For ease of identification, these instances have been bolded and centered in table 612. Eliminating these nine values leaves ninety one remaining values that are above the threshold, and permits a refined fuel score evaluation of 3.90.

Whereas FIGS. 5 and 6 conceptually show the fuel within the muscle tissue to be generally uniform, FIGS. 7-9 conceptually show the fuel within the muscle tissue as being more variable, as application of the methods has so determined in repeated testing. As such, it is advantageously beneficial for the threshold in at least one embodiment to be variable.

As suggested by the method refinement 450 for threshold evaluation, initially the threshold can be based on the previously determined general threshold for the entire scan. However, in at least one embodiment an adjustable cache for the values of areas proximate to the current area being evaluated is established. Until the cache is established, e.g., for the first few passes of evaluation, decision 452, the initial threshold value is used, block 454.

In varying embodiments this cache may be for areas in the same row (N elements before, after or on either side), areas in the same column (M elements above, below or on either side), areas in the same grid subsection (M elements by N elements including the currently selected area), and or combinations thereof. How the cache of proximate values is established—above, below, before, after, around—is largely dependent on how the areas of the scan are selected for evaluation. In addition, the number of values that may be maintained in the cache is at least in part determined by the defined size of each area.

With respect to the method refinement 450 for threshold evaluation, if the value is above the threshold, decision 458 the area and its value are kept, but the value may also be added to the proximate value cache, consisting of N members. As new members are added, old members are discarded, and in this way the proximate value cache maintains a consistent record of values for proximate areas.

Moreover, when the next area is selected, block 420 of the evaluation operation method, as the proximate cache has been established, the threshold is based on the proximate value cache, block 456. As before, in at least one embodiment, the threshold is a percentage of the proximate value cache. By adopting a percentage, some degree of fluctuation between areas is permitted, but a sudden change will stand out as tissue substantially unlikely to be muscle tissue.

Figure 13:
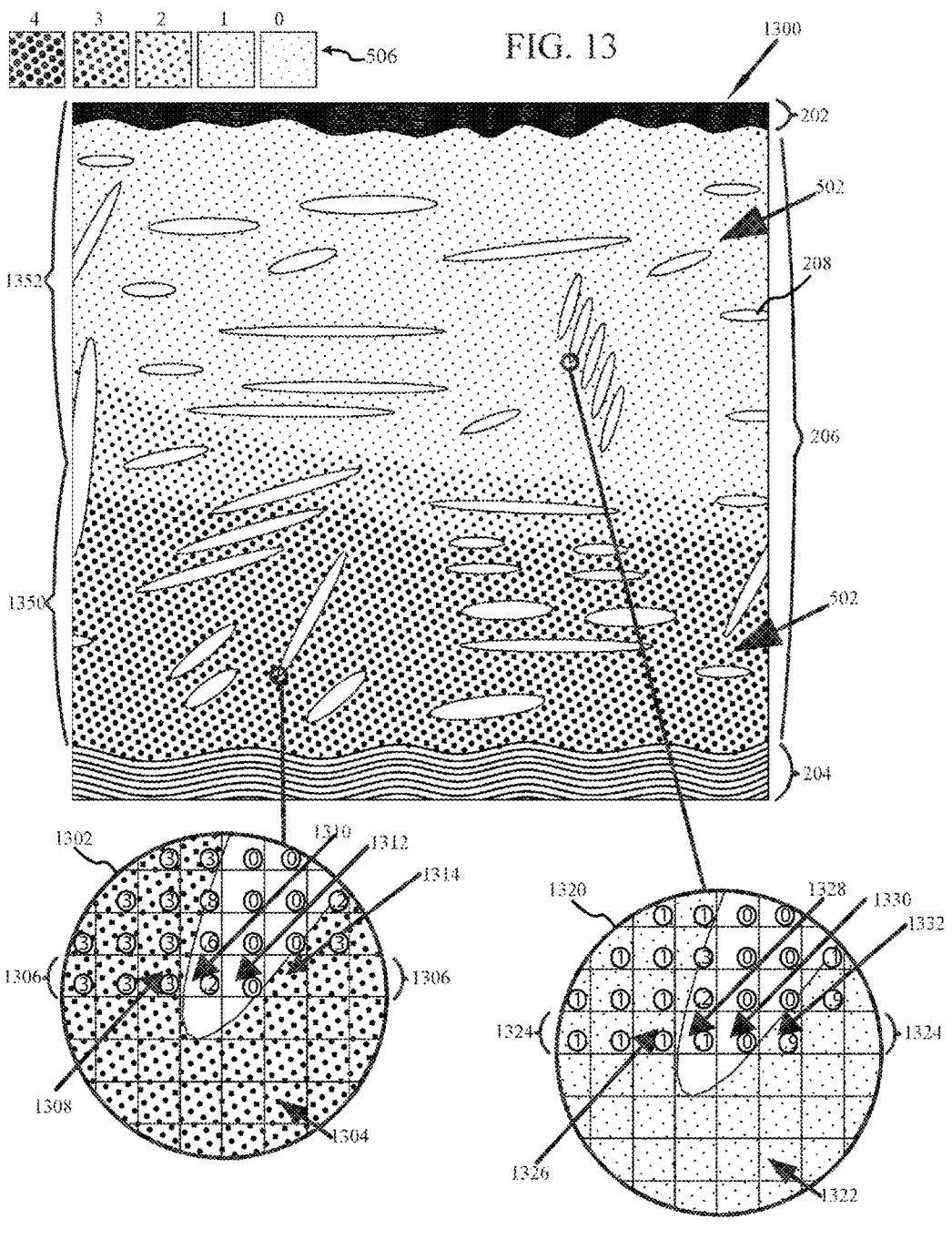
FIG. 13 is a conceptual illustration of an ultrasound scan of a target muscle further illustrating a first part having a first threshold value and a second part having a second threshold value in accordance with at least one embodiment.

FIG. 13 conceptually illustrates a scan 1300 of a target muscle 106. As with FIGS. 5-9, fuel 502 within the muscle tissue 206 are represented as dots of varying sizes. As shown in scan 1300 the deeper portion 1350 of the target muscle 106 has a greater apparent fuel amount 502 then the outer portion 1352 of the target muscle. As such, if a constant threshold was applied in the evaluation, areas in the outer portion 1352 might be inadvertently discounted and areas of the deeper portion 1350 might be inadvertently included, and or vis-a-versa depending on the value of the threshold.

An enlarged first section 1302 is shown for the deeper portion 1350. Within this enlarged section a plurality of areas 1304 are shown. These areas include muscle tissue 206, but also in some instances non-muscle tissue 208. The scale of the areas is such that as shown each area is predominantly either muscle tissue 206 or non-muscle tissue 208. With respect to the fuel concentration scale 506, the attributes of the areas of predominant muscle tissue are defined as "3" whereas the attributes of the areas of non-muscle tissue are defined as "0."

By way of example to demonstrate the application of the proximate cache value, attention is directed to example row 1306, and currently selected area 1308. The proximate value cache from the two areas immediately to the left of area 1308 are 3. As the attributes of area 1308 are also evaluated as a 3, the value of area 1308 is above the threshold, regardless of what percentage is used. Area 1308 and its value are then kept for the overall fuel determination and the value is also added to the proximate value cache, block 460. If the cache is full, the oldest value is discarded and the new value is added.

The selection of the next area is then area 1310. In this case the attributes are evaluated as, for example 0.2. If the threshold is set as 80% of the proximate value cache (e.g., 3), the threshold would be 2.4—well above the 0.2 of area 1310. Area 1310 is therefore discarded as being very likely non-muscle tissue 208, block 462. The same is true for the next area 1312. However, for the next area 1314 the attributes are evaluated as 2.8 (not shown on FIG. 13) which is above the threshold. Area 1314 is kept and the proximate value cache updated once again, block 460.

Moreover, with a sufficiently fine granularity of defined areas and a reasonable proximate value cache, non-muscle tissue 208 can be statistically identified and eliminated with a reasonable degree of accuracy.

Turning now to the enlarged second section 1320 for the outer section, it is clear that areas 1322 are of substantially the same size as areas 1304 shown in the enlarged first section 1302. It is also visually apparent that with respect to the fuel concentration scale 506 the attributes of the areas of predominant muscle tissue for the enlarged second section 1320 are defined as "1" and again the attributes of the areas of non-muscle tissue are defined as "0."

To parallel the above example, for enlarged second section 1320 attention is directed to example row 1324, and currently selected area 1326. The proximate value cache from the two areas immediately to the left of area 1326 are 1. As the attributes of area 1326 are also evaluated as a 1, the value of area 1326 is above the threshold, regardless of what percentage is used. Area 1326 and its value are then kept for the overall fuel determination and the value is also added to the proximate value cache, block 460. If the cache is full, the oldest value is discarded and the new value is added.

The selection of the next area is then area 1328. In this case the attributes are evaluated as, for example 0.1. If the threshold is set as 80% of the proximate value cache (e.g., 1), the threshold would be 0.8. While the difference between the areas value and the threshold is not as great as the similar example of the enlarged first section 1302, it is still below the threshold and therefore discarded as being very likely non-muscle tissue 208, block 462. The same is true for the next area 1330. However, for the next area 1332 the attributes are evaluated as 0.9 which is above the threshold. Area 1332 is kept and the proximate value cache updated once again, block 460.

To summarize the threshold for the enlarged first section 1302 is 2.4 whereas the threshold for the enlarged second section 1320 is 0.8, and each threshold is effective for its proximate location. Moreover, for at least one embodiment, a first part 1302 of the scan 1300 of the target muscle 106 has a first threshold value and a second part 1320 of the scan 1300 of the target muscle 106 has a second threshold value. For each, the threshold value is determined from a cache of neighboring area attribute values.

With respect to applications of SNDGS 100 and or methods 300/350/400/1900/1950, for training, conditioning, rehabilitation or other purpose, it should be understood and appreciated, that the fuel of more than one target muscle 106 can be determined. Moreover, the same muscle type, e.g. rectus femoris, vastus lateralis, biceps, etc. . . . , may be targeted in both the left and right legs or left and right arms, chest or back for comparison, and or different muscles from different areas may be compared, as is discussed further below. Further still, for each muscle there is also generally a long axis and a short axis, i.e., parallel to the subject's leg or arm bone or perpendicular to the subject's leg or arm bone. In varying embodiments, long axis and short axis scans of the same target muscle may also be compared.

FIG. 14 conceptually illustrates charts from several additional applications of SNDGS 100 and or method 300/350/400/1900/1950. In FIG. 1400A, the first, second and third fuel scans as evaluated show very little difference for the target muscle, indicating that the subject is not in a prime condition for continued training (e.g., the muscles are fatigued), and though he or she may feel fine, heavy exertion may indeed overtax the muscles, and a lesser workout or even rest may be preferable to continuing the current exercise routine.

In FIG. 1400B, a scan 1402 of a target muscle in a subject's left leg, e.g. left vastus lateralis, are plotted with the scan 1404 of a target muscle in the subject's right leg, e.g., right vastus lateralis which is shown to be similar but faster in depletion as the subject is undergoing rehabilitation.

In FIG. 14C different target muscles are plotted together, such as the rectus femoris 1406 and vastus lateralis 1408 of a subject for comparison and review of how different muscles are or are not similarly depleting their respective fuel during active use.

With respect to the above description of SNGDS 100 and methods 300, 350, 400, 1900 and 1950 it is understood and appreciated that the method may be rendered in a variety of different forms of code and instruction as may be preferred for different computer systems and environments. To expand upon the initial suggestion of a processor based device such as a computer 108 shown in FIG. 1 and discussed above, FIG. 15 is a high-level block diagram of an exemplary computer system 1500. Computer system 1500 has a case 1502, enclosing a main board 1504. The main board has a system bus 1506, connection ports 1508, a processing unit, such as Central Processing Unit (CPU) 1510 and a memory storage device, such as main memory 1512, and optionally a solid state drive or hard drive 1514 and/or CD/DVD ROM drive 1516.

Memory bus 1518 couples main memory 1512 to CPU 1510. A system bus 1506 couples hard drive 1514, CD/DVD ROM drive 1516 and connection ports 1508 to CPU 1510. Multiple input devices may be provided, such as for example a mouse 1520 and keyboard 1522. Multiple output devices may also be provided, such as for example a video display 1524 and a printer (not shown). In varying embodiments, the video display may also be a touch sensitive input device.

Computer system 1500 may be a commercially available system, such as a desktop workstation unit provided by IBM, Dell Computers, Gateway, Apple, Sun Micro Systems, or other computer system provider. Computer system 1500 may also be a smart phone or tablet computer such as an iPhone or iPad provided by Apple, the HP Slate, the Augen or Archos Android tablets, the Motorola Xoom or other such device. Computer system 1500 may also be a networked computer system, wherein memory storage components such as hard drive 1514, additional CPUs 1510 and output devices such as printers are provided by physically separate computer systems commonly connected together in the network. Those skilled in the art will understand and appreciate that physical composition of components and component interconnections comprising computer system 1500, and select a computer system 1200 suitable for the schedules to be established and maintained.

When computer system 1500 is activated, preferably an operating system 1526 will load into main memory 1512 as part of the boot strap startup sequence and ready the computer system 1500 for operation. At the simplest level, and in the most general sense, the tasks of an operating system fall into specific categories—process management, device management (including application and user interface management) and memory management.

In such a computer system 1500, the CPU 1510 is operable to perform one or more of the methods of non-invasive determination of fuel as described above. Those skilled in the art will understand that a computer-readable medium 1528 on which is a computer program 1530 for non-invasive determination of fuel may be provided to the computer system 1500. The form of the medium 1528 and language of the program 1530 are understood to be appropriate for computer system 1500. Utilizing the memory stores, such as for example one or more hard drives 1514 and main system memory 1512, the operable CPU 1502 will read the instructions provided by the computer program 1530 and operate to perform as SNDGS 100 as described above.

With respect to the various forms of the processor based device, such as the computer 108, further discussed and described as computer 1500, FIGS. 16-18 present alternative embodiments for the structural arrangement of components comprising SNDGS 100. More specifically, for alternative SNDGS 1600 as shown in FIG. 16, the ultrasound transducer 126 is coupled directly to the computer 108, such that SNDGS 1600 is itself disposed adjacent to the target muscle 106 (not shown).

For alternative SNDGS 1700 shown as FIG. 17, a dedicated processor based device such as a customized computer 1702 is provided, as opposed to adapting a pre-existing smart phone, tablet computer or other computer system. For SNDGS 1700, the display 116 of SNDGS 1600 is not shown so as to illustrate that alternative output devices such as an indicator 1704, lights 1706, speaker 1708, vibrator 1710 and/or combinations thereof can provide an operator with an indication of the non-invasively determined fuel. As with SNDGS 1600, the ultrasound transducer 126 may be directly coupled to the customized computer 1702, or tethered by a communications link 1712—wireless or wired as shown.

Further, for yet other embodiments, the computer program 112 to adapt a computer 108 may be provided directly by enhanced ultrasound transducer 1800. More specifically, computer program 112 may be incorporated as part of the circuit structure 1802 of enhanced ultrasound transducer 1800 such that upon connection to computer 108, SNDGS 100 is provided.

As suggested above with respect to FIG. 1, the computer program 112 may also be provided by a non-portable media such as a disc 114 to a third party computer, such as computer 1804, providing an application platform such as but not limited to the Apple App Store. A user can then connect his or her computer 108, such as tablet computer 1806 to the third party computer 1804 by a network 1808 (wired or wireless) or other communication channel and obtain computer program 112 so as to adapt his or her computer 1806 to perform as SNDGS 100 when a scan of a target muscle is provided. In varying embodiments, this scan may be provided by coupling computer 1806 to ultrasound transducer 126 operated as described above, receiving a scan of a target muscle from internal storage 1810, or receiving a scan of a target muscle another computer system 1812 via wired or wireless network 1814, or other appropriate communication channel.

Moreover, embodiments of SNDGS 100/1600/1700 are intended for a wide range of subjects. In many instances the primary user of SNDGS 100/1600/1700 is a coach or trainer who utilizes SNDGS 100/1600/1700 as an advantageous tool, as he or she can scan target muscles in athletes during training and test in real time at and during competition, regulations permitting, to better ensure optimum performance. Likewise with respect to civilian or military medical care, a doctor, nurse, therapist, or caregiver may utilize SNDGS 100/1600/1700 to ensure that patents under his or her care are receiving a proper balance of carbohydrates, water and muscle stimulating exercise. Further, a military commander and/or training officer can utilize SNDGS 100/1600/1700 to forecast requirements so that operating members of a team during a mission have sufficient food resources. And of course use of embodiments of SNDGS 100/1600/1700 are not strictly limited to human beings. Indeed, horse trainers, zoo veterinarians and other parties may employ the use of embodiments of SNDGS 100/1600/1700 to non-invasively determine the muscle fuel of the animals entrusted to their care.

In further embodiments, determination of a subject's muscle fuel value can be used to provide an estimated fuel level for a muscle, i.e., the relative level of fuel a muscle has at any given time, as compared to its historical fuel levels. Estimated fuel level for a muscle takes advantage of previously determined fuel value data sets for a target muscle.

Over the course of days, months, or years an indicator muscle or target muscle can be tested for fuel values and a data set established (discussed above). Once a fuel value data set has been established for the target muscle, an estimated fuel level can be determined for the muscle at that time. A newly tested, real time, or current fuel value is completed and compared to the muscle's fuel value data set and given a percent against the 100% or "full" fuel value (highest recorded fuel value from indicator muscle or target muscle data set) to 1% or "empty" fuel value (lowest recorded fuel value from the indicator muscle or target muscle data set). So for example, a muscle that shows a raw score that is 60% of the maximum or full fuel value, will have an estimated fuel level of 60% as to that visit. This score is unique to that subject and to that subject's tested or indicator muscle. The estimated fuel level is an indicator of the muscle's readiness, i.e., essentially, "is that muscle's fuel tank full?" The estimated fuel value also tracks a muscle's depletion and recovery, so for example, as described above, a second fuel value testing can be performed on the target muscle after an exercise regime to see the effects on the muscle's estimated fuel level. The depletion of the muscle's fuel level can then be used to accurately predict how the subject's muscle(s) will react to performance parameters, such that, for example, an athlete can track fuel consumption for an athletic event or military personnel can track fuel consumption for a mission.

In some embodiments, particularly where there has been a smaller number of fuel value determinations completed for a muscle, the maximum fuel value or "full tank" value is given a 75% or 80%, not 100%, of a potential fuel value reading. In this way, it allows for the recognition that additional fuel value readings could exceed the maximum tested value, for example be 87%. With additional readings, greater than 20, or 30, or 40 for example, the maximum can be reset at 100% of the muscle's fuel.

Figure 22:
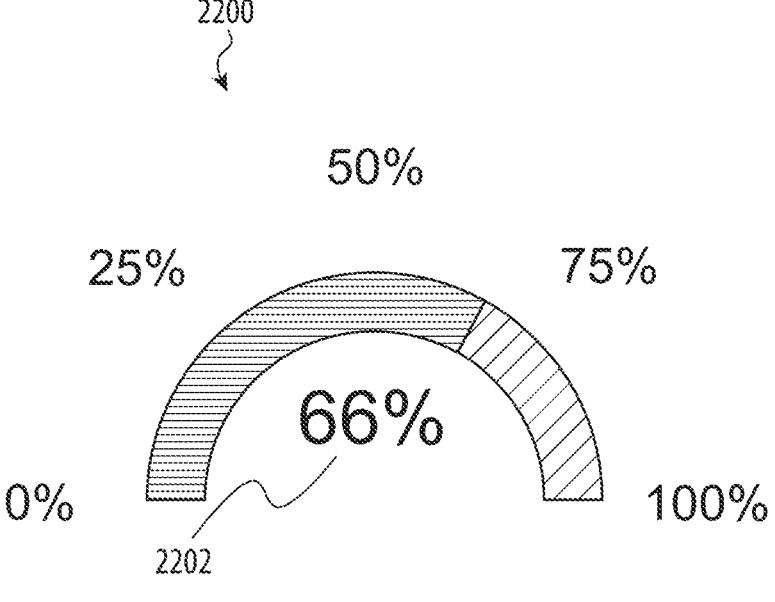
FIG. 22 illustrates a estimated fuel level score in accordance with at least one embodiment.

FIG. 22 shows one illustrative estimated fuel level schematic where the current value is like a gas gage for a fuel tank 2200. The current estimated fuel level for a muscle is shown as 66%, meaning the tested muscle has 66% of the fuel of a fully fueled (historic maximum fuel value) target muscle 2202. This estimated fuel level can be used by subjects, athletic trainers, military personnel and the like to have an accurate appreciation of their target or indicator muscle, and therefore their overall skeletal muscle systems readiness for performance. An estimated fuel level that is at 5%, 10%, or 15% would indicate that the subject should rest and re-fuel their muscles prior to any further performance based activities, where an estimated fuel level of above 50% and more typically above 75% would indicate that the subject is prepared for physical performance.

Once a muscle's estimated full level is determined, a target muscle's fuel rating may be determined. A muscle's fuel rating utilizes the same fuel values as used to identify the estimated fuel level, but compares the number to the historical fuel number for the same muscle over a past predetermined number of days, e.g., 30 days, 14 days, 7 days, etc., a period of injury, a particular age, etc., or against the same muscle in other individuals of like gender, age, athletic endeavor, profession or other linking parameter. The fuel rating can be a percent based value or can be a category based value, for example, a subject takes a real time fuel value and fuel level for a target muscle and then compares that value to a group of the same gender and age.

Figure 23:
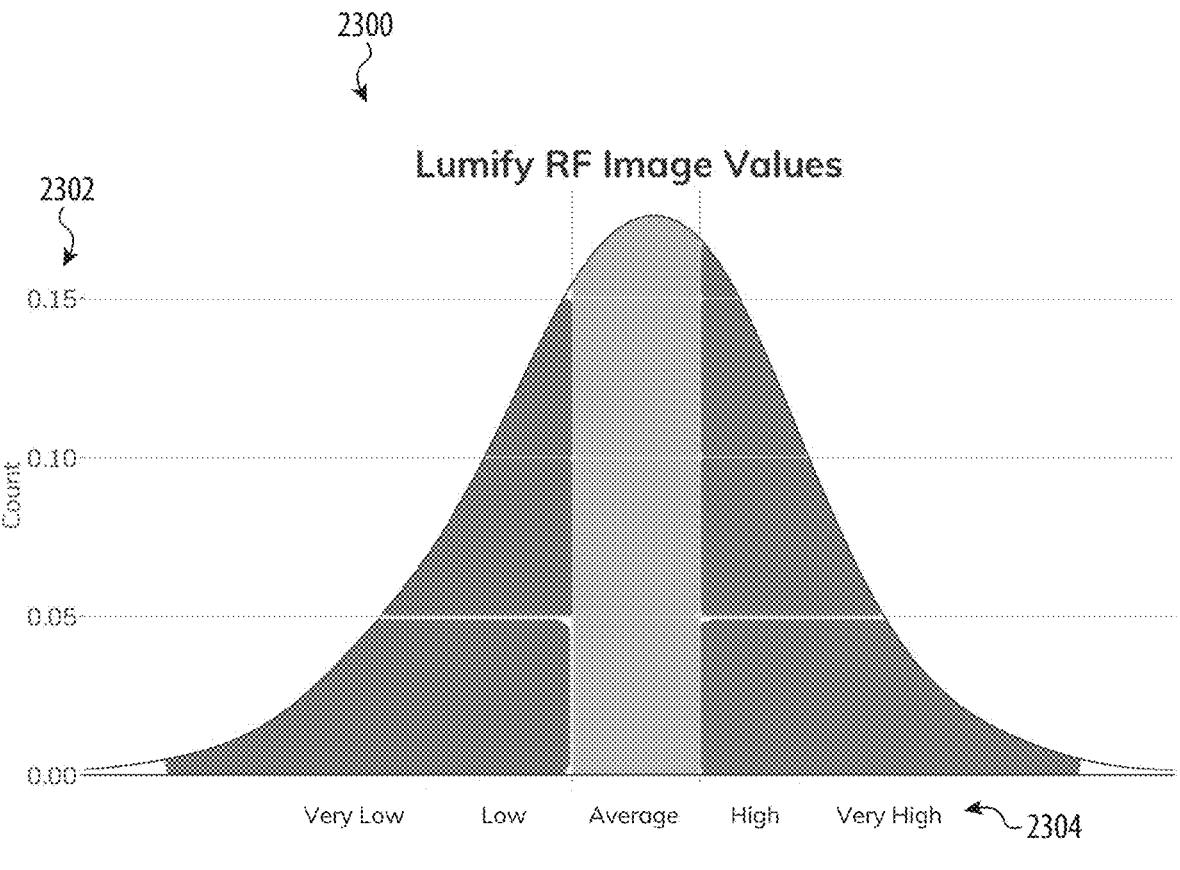
FIG. 23 illustrates a fuel rating scale and score in accordance with at least one embodiment.

As shown in FIG. 23, a data bell curve plot is used to show the fuel values created from the historical values of a number of other individuals, and the current findings plotted 2300.

The bell curve plot illustrates the muscle fuel values for the data set. In this embodiment, the fuel value or number 2302 is used to show how the muscle is currently scoring categorically (not as a percent) against the other individuals, i.e., fuel rating. So for example, is the muscle scoring in a very low, low, average, high, or very high range 2304 rating. The rating tracks long term changes, and tracks effects of changes in behavior, events (injury, overtraining, weight loss or gain, . . . ) and potential.

The fuel rating can also be determined by comparing the muscle's fuel value to other like target muscles in like individuals, for example, rate the subject's raw score against an individual having the same gender and age, or against an individual involved in the same athletic endeavor, e.g., rate the fuel level of the muscle for a bicep of a 18 year old pitcher against the bicep of another 18 year old pitcher, on the same or competing team. Perhaps, the 18 year old has a bicep with a bicep fuel rating that is average against its own historical numbers, but low against other like pitchers of similar age and gender. This data allows for comparisons and allows for the question, how do my muscles compare to myself historically, or alternatively, how do my muscles compare to others who have been assessed in the same way? As noted above, the rating can be based on a category (very low, low, average, etc.) or can be a percentile, your target muscle fuel rating is 60% that of other 30 year old female cyclists in the data set.

The data set for fuel values for a muscle can be increased or decreased. As such, the range for use in determining a target muscle's fuel status can be dynamic, as more data points (fuel values) provides for more accurate determinations. It is also envisioned that ranges can be established for particular uses, for example, a data set range used for a subject during exercise only, at a particular age, or during a period of target muscle injury, and the like. In some embodiments, two or more data points can be used to establish the range of fuel values, three or more, four or more, five or more, six or more, seven or more, and the like. In some embodiments, a statistical confidence number can be shown as part of the estimated fuel level, so for example, where enough data points exist, the fuel level could be reported as 71% with 95% confidence.

In at least one other embodiment, the systems and methods described herein can be used to rate an energy status of one or more muscles in a subject. As used herein, "muscle energy status" or "energy status" is a scoring value that indicates the performance readiness of a targeted muscle or of a subject's entire muscle system. In order to determine a muscle's performance readiness, the measured fuel value for the muscle is determined and quantified versus that same muscle's overall capacity (fuel tank), and is then compared to other individual's fuel levels for the same muscle, i.e., the muscle's fuel rating. The scoring of the fuel level and fuel rating are combined to give an overall muscle energy status. The muscle energy status is a composite of these two measurements, represented as: muscle energy status=(fuel level+fuel rating)/2. The resulting number provides an excellent composite determination as to the muscle's overall capacity to perform. A number of different score scales can be used to signify the muscle's energy status. In one aspect, a composite score of 0-33 indicates that the muscle energy status is low or red, 34-66 indicates that the muscle energy status is average or teal, and a muscle energy score of 67-100 indicates that the muscle energy status is high or green. Alternatively, rate of occurrence for a muscle's energy status can be used, where a muscle's energy status over time is plotted and real time numbers compared to those values.

Here, the subject's historic muscle energy status provides the result of the composite score. Based on the inventor's findings, this scale has provided a 0-44 energy score as being in the bottom third of most subject's muscle energy status, so this would be the low or red status, 45-62 energy score is in the middle third of most subject's energy status, so this would be the average or teal score, and 63-100 is the top third of most subject's muscle energy status, so this would be the high or green status.

Figure 24:
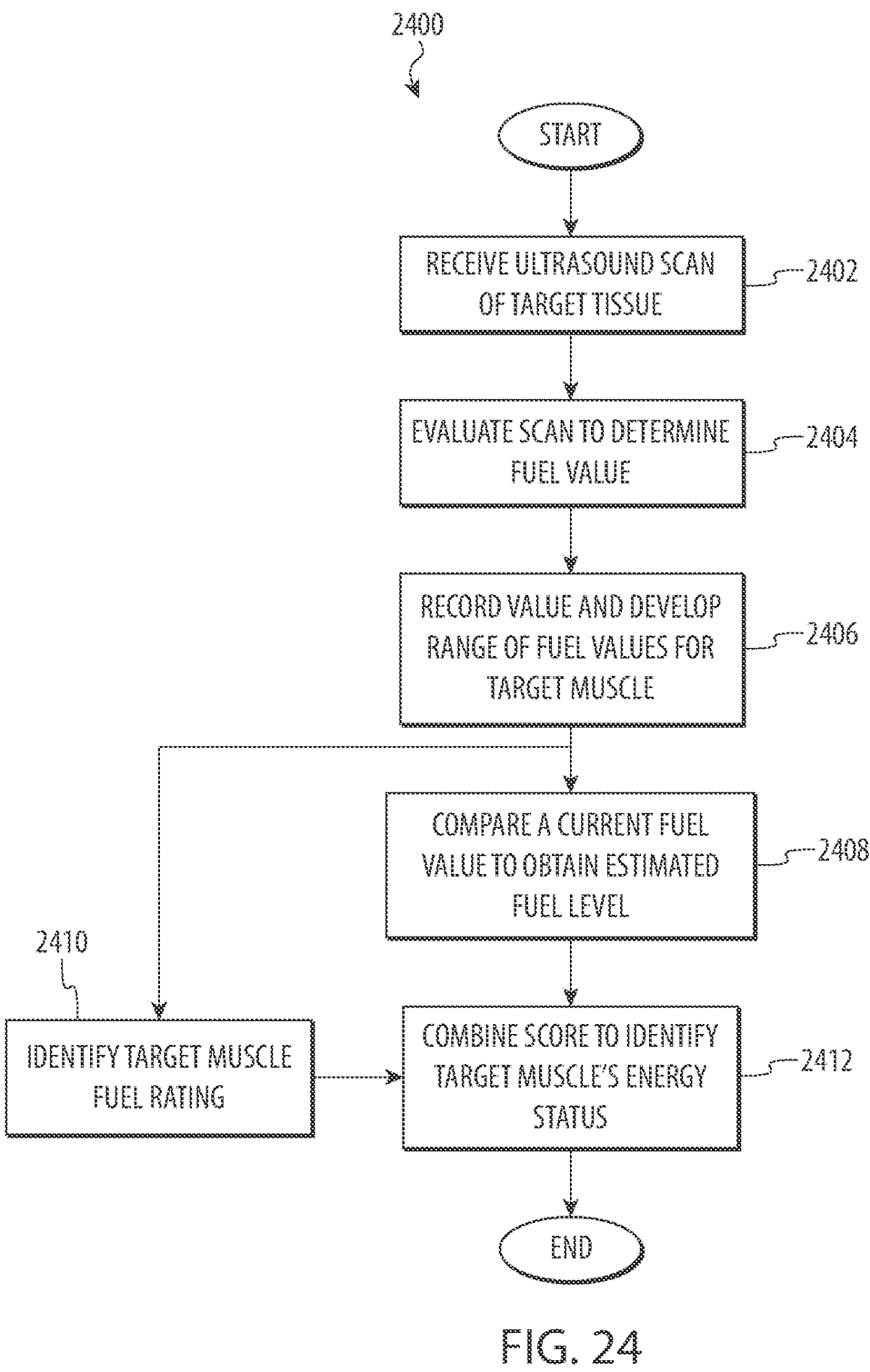
FIG. 24 illustrates a flow chart for determining muscle energy status in accordance with at least one embodiment.

FIG. 24 is a flow diagram in accordance with an embodiment for determining a target muscle's energy status 2200. A muscle's energy status is a composite value made up of the estimated fuel level and muscle fuel rating. A fully fueled and well rated muscle is at a high muscle energy status, and can be used for monitoring optimal levels of readiness for, as well as recover from, exercise. The method in FIG. 24 begins by scanning a target muscle as described herein to receive an ultrasound scan 2402. As in previous methods, the scan is evaluated to determine a fuel value 2404. The fuel value is recorded as an element of a data set for the target muscle. A range of fuel values is obtained for the muscle over a course of time and/or visits. Once a sufficient number of fuel values has been obtained, a range of values is established 2206. In typical embodiments, the range corresponds to the minimum fuel value and the maximum fuel value, and all values in between, e.g., the minimum fuel value can be scored as a 0 or 1 and the maximum fuel value is scored as a 100 (or 80 as described above). As can be envisioned by those of skill in the art, other scoring scales can be used, and a 1 to 100 is for illustrative purposes only. The fuel level is then compared to a fuel rating of use for the particular subject, for example, the same muscle for the same gender and age, to give a muscle fuel rating.

Again referring to FIG. 24, once an estimated fuel level and fuel rating have been determined, the target muscle's energy status is determined 2412. The composite value, for example, 60% estimated fuel level and 50% fuel rating, result in the energy status for the muscle. The combined results can be used to provide a numerical value (55, for example), or a status value (55 results in a yellow reading, for example). A muscle's energy status is an indicator of a muscle's performance readiness, particularly, a muscle's full performance readiness. A muscle that is high in estimated fuel (60% or above) and fuel rated at "above average", is a muscle that can be trusted to engage in activity and exercise with high likelihood of positive results and low likelihood of use injuries. Conversely, an estimated fuel of below 50% and rated at below 33% ("low" or "very low"), can be expected to perform sub-optimally, for example. The numeric score can be based on a matrix or other useful combination score, and the range itself can include any number of values, e.g., 1-4, 1-5, 1-10, 1-50, 1-100 for example.

As can be imagined, testing of athletes just prior to an event or game provides a strong advantage as players can be replaced with other athletes having optimal performance readiness. For example, a running back for the local football team may have muscle energy status for his lower body muscles that all rate at in the 3-5 range out of 10, whereas his replacement may show the same muscle groups as being in the 7-9 range out of 10. The coach may insert the replacement running back, given his higher muscle performance readiness.

Figure 25:
FIG. 25 illustrates a series of muscle energy status scores for a subject over the course of several months in accordance with at least one embodiment.

FIG. 25 shows an illustrative muscle energy status chart tracking a subjects numeric score over the course of 7 months 2500. The historic data can be combined or compared to changes in exercise routines, weight, age, and the like. A subject may have various muscle energy status charts, one prepared before exercise and one prepared after exercise, for example.

Figure 26:
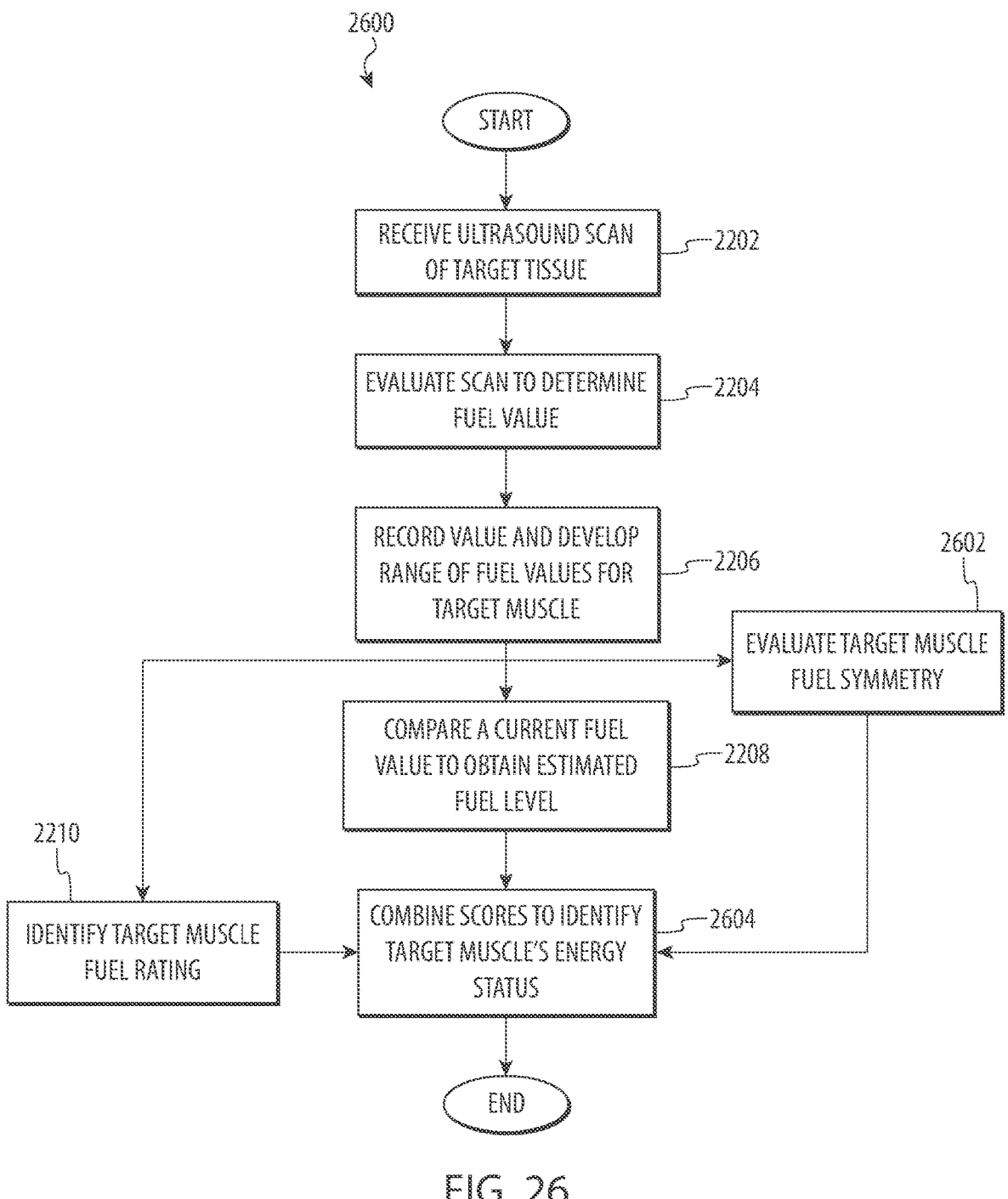
FIG. 26 illustrates an alternative flow chart for determining muscle energy status in accordance with at least one embodiment.
Figure 27:
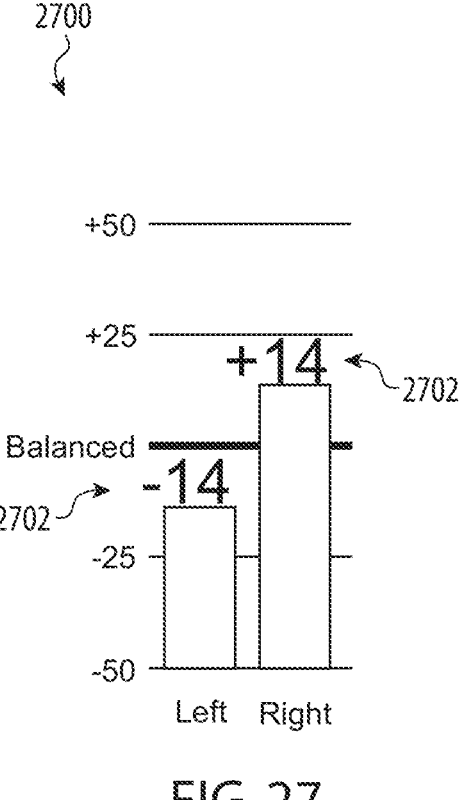
FIG. 27 illustrates a fuel symmetry score in accordance with at least one embodiment.
Figure 28A:
FIG. 28A-D illustrate one possible muscle energy readout for a subject in accordance with at least one embodiment.
Figure 28B:
Figure 28C:
Figure 28D:
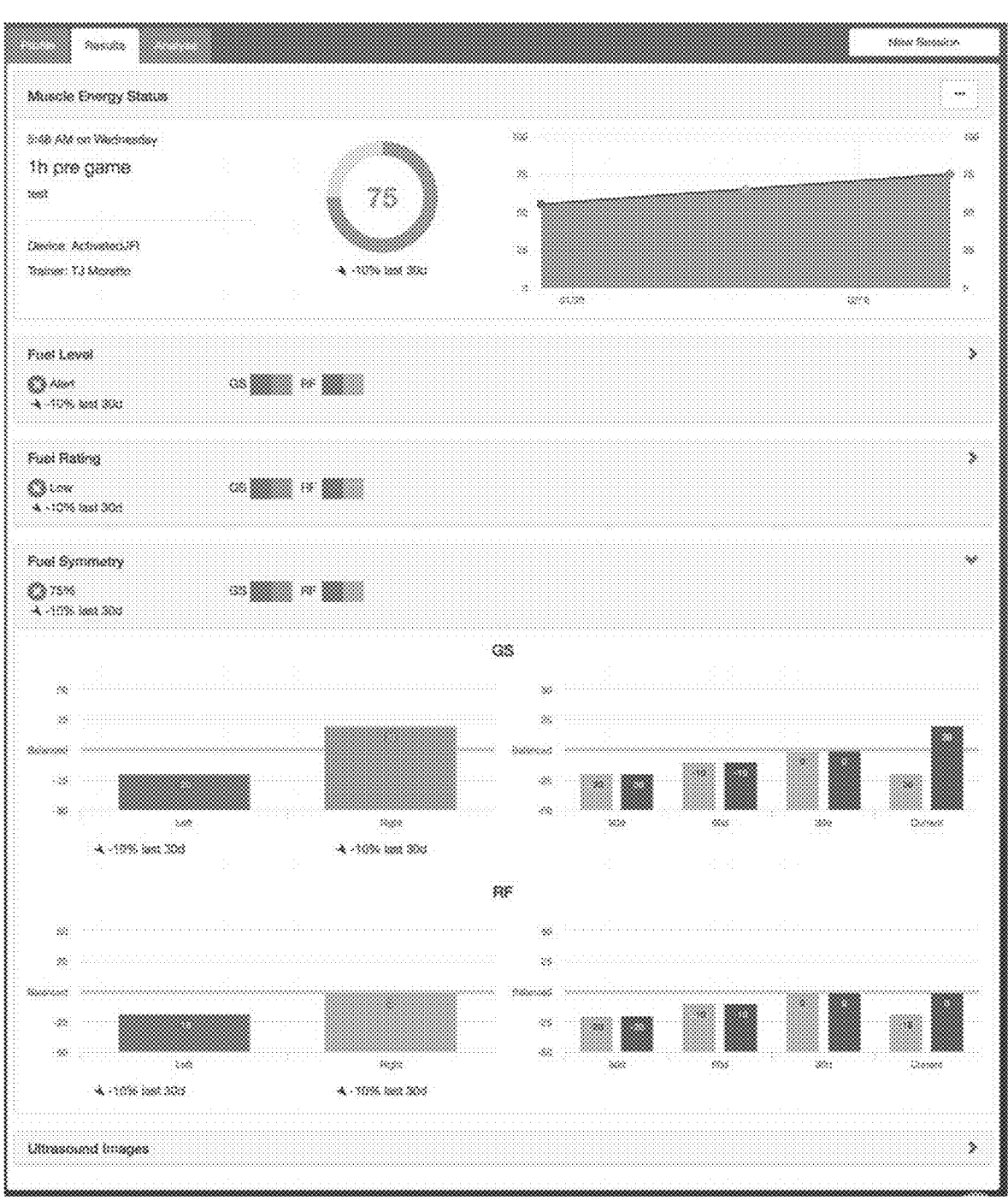

FIG. 26 is a flow diagram in accordance with another embodiment for determining a muscle's energy status 2600. The method includes steps 2202, 2204, 2206, 2208 and 2210, in combination with an evaluation of the target muscle's fuel symmetry 2602. In this method, the target muscle fuel value is also compared to the fuel value for the target muscle's symmetrical partner in the subject, i.e., between contralateral muscles. So for example, the fuel value of a subject's right bicep is compared to the fuel value of the subject's left bicep. A comparison between the two symmetrical muscles is obtained and the difference determined. The fuel symmetry is a +/–value, based on the difference between the two symmetrical muscles. FIG. 27 provides an illustrative schematic of a target muscle, left and right side 2700. In this example, the fuel symmetry of +/–14, meaning that the right muscle has a 14% higher fuel level than the left target muscle 2702. The comparison can be performed using the raw fuel value for the current scan, or, more typically, performed using the estimated fuel level (as discussed above). In typical embodiments, the estimated fuel level is compared. A balanced fuel symmetry for a target muscle is a good indicator that the muscle is operating with low injury risk and no performance deficits (the read-out in this case would be 0). A high imbalance, possibly due to an injury in the target muscle, provides an additional scoring aspect to the target muscle's energy status. The fuel symmetry for a subject can also be determined for a group of muscles, for example, compare the fuel symmetry for all muscles in a subject's right arm versus for the subject's left arm. These comparisons can also be used to track trends, particularly where injury and injury recovery are involved.

The combination of the three target muscle testing elements: estimated fuel level, fuel rating, and optionally, fuel symmetry, provide the muscle energy status for any given target muscle or group of muscles in a subject 2604. The overall energy status therefore takes into account the present fuel value for the muscle, how that muscle rates against itself or other like situated muscles, and how that muscle rates against its' symmetrical partner.

FIG. 28A-28D show four illustrative muscle energy status reports for a target muscle. Each illustration comes with different levels of information and feedback for the subject.

Figure 29:
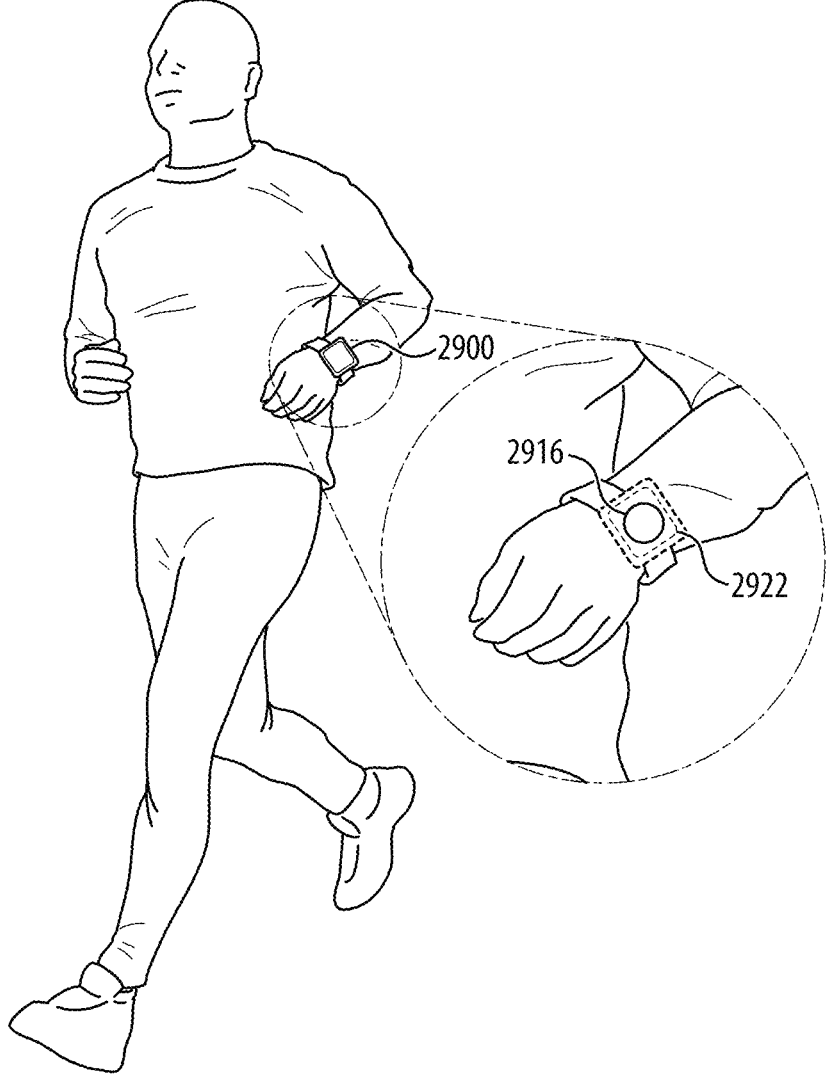
FIG. 29 depicts a conceptual illustration of a fourth alternative configuration for a system for non-invasive tissue evaluation that may be used to determine human pennation angle and/or fascicle length in accordance with at least one embodiment.

As shown in FIG. 29, in some embodiments, the methods as described herein may be embodied as a wearable device, such as a smart watch or other device operable to couple around a user's body part. The devices may include a transducer 2916 positioned adjacent the user in order to obtain scans and/or other data at a variety of different times, such as during a user's workout. The devices 2900 may also include a display 2922 for providing real time and/or other analysis information to the user.

Figure 30:
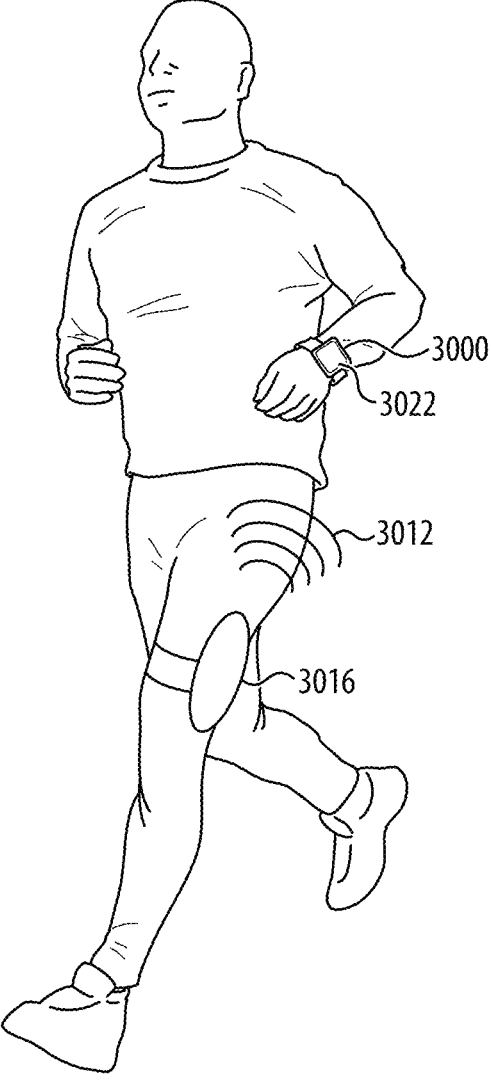
FIG. 30 depicts a conceptual illustration of a fifth alternative configuration for a system for non-invasive determination of human pennation angle and/or fascicle length in accordance with at least one embodiment.

As shown in FIG. 30, in other embodiments, a wearable device 3000 may be used with a separately wearable transducer 3016. In this way, the device 3000 may be coupled around one body part while the transducer 3016 obtains one or more scans related to tissues located in another body part. The device 3000 may receive data regarding such scans from the transducer 3016, such as wirelessly 3012, and provide real time and/or other analysis information to the user via a display 3022, for example a target muscle's current energy status.

Figure 31:
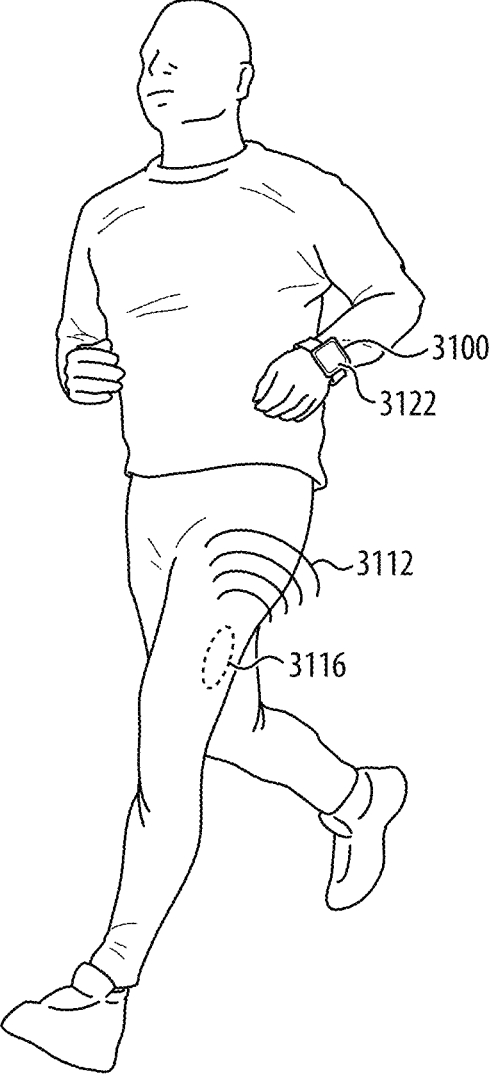
FIG. 31 depicts a conceptual illustration of a sixth alternative configuration for a system for non-invasive determination of human pennation angle and/or fascicle length in accordance with at least one embodiment.

As shown in FIG. 31, in still other embodiments, a wearable device 3100 may be used with a transducer implant 3116 located inside the user's body. In this way, the device

3100 may obtain one or more scans related to tissues located in the body without requiring attachment and positioning of a transducer for use. The device 3100 may receive data regarding such scans from the transducer implant 3116, such as wirelessly 3112, and provide real time and/or other analysis information to the user via a display 3122.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall there between.

What is claimed is:

1. A method, comprising:
developing a fuel profile for a target muscle by:
obtaining a first ultrasound scan of the target muscle, using at least one processor, when the target muscle is in a first fuel state;
evaluating the first ultrasound scan, using the at least one processor, to determine a first fuel value;
obtaining a second ultrasound scan of the target muscle, using the at least one processor, when the target muscle is in a second fuel state; and
evaluating the second ultrasound scan, using the at least one processor, to determine a second fuel value;
obtaining a current ultrasound scan of the target muscle using the at least one processor;
establishing a current fuel value for the target muscle using the at least one processor; and
ranking the current fuel value within the fuel profile to determine a current fuel level for the target muscle using the at least one processor.

2. The method of claim 1, wherein the target muscle is in the first fuel state prior to use of the target muscle.

3. The method of claim 2, wherein the target muscle is in the first fuel state after use of the target muscle.

4. The method of claim 1, wherein developing the fuel profile for the target muscle further comprises obtaining at least one additional ultrasound scan.

5. The method of claim 4, wherein developing the fuel profile for the target muscle further comprises evaluating the at least one additional ultrasound scan to determine at least one additional fuel value.

6. The method of claim 1, further comprising providing a recommendation based on the current fuel level.

7. The method of claim 1, further comprising providing a recommendation based on the current fuel value.

8. A method, comprising:
developing a fuel profile for a target muscle by:
obtaining a series of ultrasound scans of the target muscle, using at least one processor, at a number of times corresponding at least to the target muscle being in a first fuel state and the target muscle being in a second fuel state; and
evaluating the series of ultrasound scans, using the at least one processor, to determine a range of fuel values;
obtaining a current ultrasound scan of the target muscle using the at least one processor;
establishing a current fuel value for the target muscle using the at least one processor; and ranking the current fuel value within the fuel profile to determine a current fuel level for the target muscle, using the at least one processor.

9. The method of claim 8, wherein the target muscle is in the first fuel state prior to nutrition intake.

10. The method of claim 9, wherein the target muscle is in the second fuel state after nutrition intake.

11. The method of claim 8, wherein the target muscle is in:

the first fuel state prior to a passage of time since use of the target muscle; and the second fuel state after the passage of time since use of the target muscle.

12. The method of claim 8, wherein developing the fuel profile further comprises dividing the range of fuel values.

13. The method of claim 8, further comprising tracking the current fuel level over time.

14. The method of claim 8, further comprising providing the current fuel level.

15. A method, comprising:

developing a fuel profile for a target muscle by:

obtaining a series of ultrasound scans of the target muscle, using at least one processor, at a number of times corresponding at least to the target muscle being in different fuel states; and evaluating the series of ultrasound scans, using the at least one processor, to determine a range of fuel values; and determining a current fuel level for the target muscle, using the at least one processor, using a current ultrasound scan of the target muscle and the fuel profile.

16. The method of claim 15, wherein developing the fuel profile for the target muscle further comprises determining to obtain at least one additional ultrasound scan.

17. The method of claim 16, wherein developing the fuel profile for the target muscle further comprises evaluating the at least one additional ultrasound scan to determine at least one additional fuel value.

18. The method of claim 15, wherein a processing unit tracks the target muscle over time.

19. The method of claim 15, wherein developing the fuel profile for the target muscle further comprises obtaining a threshold number of ultrasound scans.

20. The method of claim 15, further comprising determining an additional current fuel level for a different muscle using a current ultrasound scan of the different muscle and the fuel profile.

\* \* \* \* \*